US012746388B2

(12) United States Patent
Abdolahad et al.

(10) Patent No.: US 12,746,388 B2
(45) Date of Patent: Sep. 29, 2026

(54) ELECTROPORATION/ ELECTROCHEMOTHERAPY OF SURGICALLY SENSITIVE REGIONS

(71) Applicants: Mohammad Abdolahad, Tehran (IR); Mohammad Ali Khayamian, Tehran (IR); Hamed Abadijoo, Tehran (IR); Farshid Rostami Pouria, Tehran (IR); Majid Hasanloo, Tehran (IR); Hossein Simaee, Tehran (IR); Navid Manoochehri, Tehran (IR); Seyed Mojtaba Yazdanparast, Tehran (IR); Alvand Naserghandi, Tehran (IR); Kosar Namakin, Tehran (IR); Seyed Rouhollah Miri, Tehran (IR); Habibollah Mahmoodzadeh, Tehran (IR); Sepideh Mansouri, Tehran (IR)

(72) Inventors: Mohammad Abdolahad, Tehran (IR); Mohammad Ali Khayamian, Tehran (IR); Hamed Abadijoo, Tehran (IR); Farshid Rostami Pouria, Tehran (IR); Majid Hasanloo, Tehran (IR); Hossein Simaee, Tehran (IR); Navid Manoochehri, Tehran (IR); Seyed Mojtaba Yazdanparast, Tehran (IR); Alvand Naserghandi, Tehran (IR); Kosar Namakin, Tehran (IR); Seyed Rouhollah Miri, Tehran (IR); Habibollah Mahmoodzadeh, Tehran (IR); Sepideh Mansouri, Tehran (IR)

( * ) Notice: Subject to any disclaimer, the term of this patent is extended or adjusted under 35 U.S.C. 154(b) by 0 days.

(21) Appl. No.: 18/689,231

(22) PCT Filed: Aug. 26, 2023

(86) PCT No.: PCT/IB2023/058455
§ 371 (c)(1),
(2) Date: Mar. 5, 2024

(87) PCT Pub. No.: WO2025/046258
PCT Pub. Date: Mar. 6, 2025

(65) Prior Publication Data
US 2026/0158268 A1 Jun. 11, 2026

(51) Int. Cl.
*A61N 1/32* (2006.01)
*A61N 1/04* (2006.01)

(52) U.S. Cl.
CPC ........... *A61N 1/327* (2013.01); *A61N 1/0412* (2013.01)

(58) Field of Classification Search
CPC .............................. A61N 1/327; A61N 1/0412
See application file for complete search history.

*Primary Examiner* — Serkan Akar

(57) ABSTRACT

Disclosed herein are devices for in-vivo electroporation of target cells in sensitive and/or difficult-to-access regions of a living body and systems and methods utilizing thereof. The devices include non-invasive structured electrodes placed at a target region or in the vicinity of the target region without causing bleeding, tearing, or any injuries. The target cells are electroporated by applying at least one sequence of electric voltage pulses between the non-invasive structured utilizing an electrical pulse generator. An electroporation process may be assisted by tracking and adjusting a location of one or more electrodes of the devices utilizing a camera attached to the one or more electrodes placed inside the target region. An electroporation process may be assisted by tightening a contact between one or more electrodes of the devices and the target region by pulling the target region towards the one or more electrodes utilizing a vacuum pressure generator.

19 Claims, 16 Drawing Sheets

ELECTROPORATION/ ELECTROCHEMOTHERAPY OF SURGICALLY SENSITIVE REGIONS

CROSS-REFERENCE TO RELATED APPLICATION

This application is a national stage of PCT/IB2023/058455 filed Aug. 26, 2023, entitled "ELECTROPORATION/ELECTROCHEMOTHERAPY OF SURGICALLY SENSITIVE REGIONS," which is incorporated herein by reference in its entirety.

TECHNICAL FIELD

The present disclosure generally relates to methods and apparatus for target cells' ablation and/or delivery of therapeutic agents into a target cell via an electroporation process, and particularly, to electrodes with a designed structure appropriate for applying electroporation to target cells located in sensitive regions or areas of a patient's body which are difficult to access and use thereof.

BACKGROUND ART

Minimally invasive treatments are newly emerged methods that have recently been able to replace conventional surgical methods in some cases of cancer treatment, such as methods based on use of ultrasonic waves that destroy tumors by stimulating mechanical waves, or methods based on heat that heat a tumor at a target position and cause it to disappear. Radiofrequency (RF) methods are examples of heating methods in which high frequency electromagnetic waves are used. Each of these methods has prominent features and on the other hand has certain disadvantages, for example, heating-based methods cannot be used near main vessels due to a destruction of intercellular matrix. On the other hand, chemotherapy-based methods also cause problems for a patient. One of the biggest and most common problems in cancer chemotherapy is side effects of drugs on healthy tissues and creation of physiological problems in vital organs of body. Many cancer deaths are due to side effects of chemotherapy drugs on vital organs of body. Today, one of the most important areas of research in cancer treatment is construction of targeted drug delivery systems to tumor areas that cause minimal damage to healthy body tissues.

One of the minimally invasive newly proposed methods is treatment of cancer based on electroporation. In this method, holes are created on cancer cells by applying high voltage electrical pulses, which cause permeability of cancer cells. Holes created by electroporation may have different life-times based on their size, and larger holes may last longer. Pore lifetime spans from milliseconds to hours. Holes with long life-times (more than a few hours) may disrupt the tissue homeostasis and result cell death. Depending on an amount of generated electrical field and a duration of electrical pulse, the holes created on cells can be reversible, and as a result, the hole closes after the end of electrical pulse application, and finally, cells will survive. This method is used to deliver more chemotherapy drugs to tumor cells named as electrochemotherapy (ECT) since considerable enhances the efficiency of local chemotherapy. In another case, in which a created hole on cells membrane is such that the cells cannot close it, it is called irreversible electroporation and is done to directly tumor removal without mediation of chemotherapy drugs, which is also called irreversible electroporation (IRE). Depending on type of mass and its location, and many other parameters, treatment can be done in form of ECT or IRE. In this method, high voltage electrical pulses are applied to target cancer cells or cancerous tissue in a short period of time, which leads to a disruption of ionic potential balance of cell membrane; thereby, resulting in generating holes on cells and increasing permeability of cells.

Needle-based electrodes are mostly used for electroporation treatments, and many improvements and efforts have been made to fabricate and utilize electroporation devices having needle electrodes. For example, A. Westersten et al. disclosed in a US patent application numbered as US 2006/0264807 A1 a modular electrode system including a non-symmetrically arranged plurality of needle electrodes, in which a constant-current electrical pulse is applied to the plurality of needle electrodes. The modular electrode system may facilitate delivery of electrical energy to tissues in a manner that assures that the energy dose delivered lies consistently between an upper limit a lower limit; thereby, providing increased electroporation efficiencies. However, conventional electrodes that are mostly utilized in electrochemotherapy have many drawbacks and design weaknesses. For example, conventional needle electrodes cannot be used in sensitive tissues, such as vessels, nerves, intestines, etc. due to bleeding in tissues and/or perforation of vital organs. On the other hand, plate electrodes are not effective in applying electrochemotherapy stimulation due to a lack of a proper interaction surface between tissue and electrode. Moreover, in many cases, a physician is dealing with spaces where it is not possible to apply electrochemotherapy stimulation due to a lack of a proper access.

Hence, there is a need in the art to overcome the problems and drawbacks of electrodes utilizing in an electroporation-based treatment. There is a need in the art for electroporation devices having less-invasive, and preferably, non-invasive electrodes. Specifically, there is a need for a device with electrodes to apply electroporation to cells, which have a structure that minimizes a possibility of damage and bleeding to sensitive tissues (including vascular tissues, nervous tissues, etc.). Also, there is a need for electrodes that allow access to areas that cannot be reached with conventional electrodes.

SUMMARY OF THE DISCLOSURE

This summary is intended to provide an overview of the subject matter of this patent, and is not intended to identify essential elements or key elements of the subject matter, nor is intended to be used to determine the scope of the claimed implementations. The proper scope of this patent may be ascertained from the claims set forth below in view of the detailed description below and the drawings.

In one general aspect, the present disclosure is directed to a system for superficial electroporation. In an exemplary embodiment, the system may include a vacuum-assisted superficial electroporation probe, an electrical pulse generator electrically connected to the vacuum-assisted superficial electroporation probe, a vacuum device connected to the vacuum-assisted superficial electroporation probe, and a processing unit electrically connected to the electrical pulse generator and the vacuum pressure generator.

In an exemplary embodiment, the vacuum-assisted superficial electroporation probe may include an electrode mounting support and at least two electrodes. In an exemplary embodiment, the electrode mounting support may include an enclosed container. In an exemplary embodiment, the electrode mounting support may include a top side and a bottom side. In an exemplary embodiment, the top side may include a singular hole and a plurality of pairs of holes and the bottom side may include a plurality of apertures. In an exemplary embodiment, each aperture of the plurality of apertures may be aligned to one of the singular hole and a pair of holes of the plurality of pairs of holes. In an exemplary embodiment, each pair of holes of the top side and the corresponding aperture of the bottom side may receive one electrode passing there through. In an exemplary embodiment, a path extending along the singular hole and an aperture of the plurality of apertures located along with the singular hole may form a hollow path. In an exemplary embodiment, the hollow path may be utilized for applying a vacuum pressure there through.

In an exemplary embodiment, each electrode of the at least two electrodes may include a wire blade protruding out from the bottom side of the electrode mounting support through an aperture of the plurality of apertures. In an exemplary embodiment, each wire blade may include a U-shaped wire comprising a flat base with two parallel lateral edges extending upwards from the flat base. In an exemplary embodiment, the two parallel lateral edges may include a first lateral edge and a second lateral edge. In an exemplary embodiment, a first lateral edge of the two parallel lateral edges may pass through a first hole of a pair of holes of the plurality of pairs of holes and a second lateral edge of the two parallel lateral edges may pass through a second hole of the pair of holes of the plurality of pairs of holes. In an exemplary embodiment, an electrically conductive wire may be welded to a first free end of the U-shaped wire and a second free end of the U-shaped wire may be fixed onto the top side of the electrode mounting support. In an exemplary embodiment, the at least two electrodes may be utilized to transfer a pulsed electric field to a plurality of target cells by putting the flat base of the wire blade of each electrode in contact with a zone of a tissue comprising the plurality of target cells.

In an exemplary embodiment, the electrical pulse generator may be electrically connected to the at least two electrodes. In an exemplary embodiment, an end of the electrically conductive wire welded to each electrode may be connected to the electrical pulse generator. In an exemplary embodiment, the electrical pulse generator may be utilized to apply a pulsed electric field to the at least two electrodes of the vacuum-assisted superficial electroporation probe.

In an exemplary embodiment, the vacuum device may include a vacuum tube and a vacuum pressure generator connected to the vacuum-assisted superficial electroporation probe via the vacuum tube. In an exemplary embodiment, the vacuum tube may include a flexible tube. In an exemplary embodiment, the vacuum tube may include a proximal end and a distal end. In an exemplary embodiment, the distal end may be fixed at a location on top of the hollow path. In an exemplary embodiment, the vacuum tube may be utilized to transfer a suction pressure to the plurality of target cells while the flat base of the wire blade of each electrode may be in contact with the zone of the tissue. In an exemplary embodiment, the proximal end of the vacuum tube may be connected to the vacuum pressure generator. In an exemplary embodiment, the vacuum pressure generator may be utilized to apply the suction pressure through the vacuum tube.

In an exemplary embodiment, the processing unit may include a memory having processor-readable instructions stored therein and a processor. In an exemplary embodiment, the processor may access the memory and execute the processor-readable instructions. In an exemplary embodiment, the processor may be utilized to perform a method when the processor-readable instructions are executed by the processor. In an exemplary embodiment, the method may include tightening a contact between the respective flat bases of the at least two electrodes and the zone of the tissue by pulling the zone of the tissue towards the at least two electrodes via applying a vacuum pressure onto the zone of the tissue utilizing the vacuum pressure generator and inducing electroporation to the plurality of target cells by applying at least one sequence of electric voltage pulses between the at least two electrodes utilizing the electrical pulse generator.

In an exemplary embodiment, the wire blades of the at least two electrodes may be in parallel relation to each other with a distance in a range of 0.5 cm to 1.5 cm from each other. In an exemplary embodiment, the flat base of each wire blade may have a length in a range of 0.5 cm to 1.5 cm. In an exemplary embodiment, a length in a range of 0.1 mm to 0.5 mm of each lateral edge of the two parallel lateral edges may protruded out from the bottom side of the electrode mounting support. In an exemplary embodiment, the U-shaped wire may include a biocompatible electrically conductive wire with a diameter in a range of 0.5 mm to 3 mm.

In an exemplary embodiment, the singular hole may be located at a center of the top side of the electrode mounting support. In an exemplary embodiment, the aperture of the plurality of apertures along with the singular hole may be located at a center of the bottom side of the electrode mounting support.

In an exemplary embodiment, the system may further include a cap that may be fixed on top of the electrode mounting support. In an exemplary embodiment, the cap may include a first outlet receiving the electrically conductive wire passing there through, a second outlet receiving the vacuum tube being fixed thereon, and a bottom surface receiving the electrically conductive wire passing there through. In an exemplary embodiment, the bottom surface may include an opening located along with the hollow path and the second outlet.

In an exemplary embodiment, applying the vacuum pressure onto the zone of the tissue may include applying a vacuum pressure with a magnitude in a range of −0.5 bar to −0.7 bar at the proximal end of the vacuum tube utilizing the vacuum pressure generator.

In an exemplary embodiment, applying the at least one sequence of electric voltage pulses between the at least two electrodes may include applying at least one sequence of eight square-wave electric voltage pulses with a magnitude in a range of 500 V/cm to 1500 V/cm and a duration of 100 μs between the at least two electrodes.

In one general aspect, the present disclosure is directed to a system for in-vivo electroporation of a plurality of target cells in a target region of a living body. In an exemplary embodiment, the system may include an electroporation device, an electrical pulse generator electrically connected to the electroporation device, and a processing unit electrically connected to the electrical pulse generator. In an exemplary embodiment, the electroporation device may be utilized to transfer a pulsed electric field to the plurality of target cells. In an exemplary embodiment, the electroporation device may include a flexible electrode and a plate electrode. In an exemplary embodiment, the flexible electrode may include a string of a plurality of spherical magnets connected in series. In an exemplary embodiment, the flexible electrode may have a variable length. In an exemplary embodiment, the variable length of the flexible electrode may be adjustable by adding or removing one or more spherical magnets to/from the string of the plurality of spherical magnets. In an exemplary embodiment, the flexible electrode may be put inside the living body in the vicinity of the target region. In an exemplary embodiment, the plate electrode may be put in the vicinity of the target region. In an exemplary embodiment, the plate electrode may include a plate magnet or a ferromagnetic steel plate. In an exemplary embodiment, the flexible electrode may be movable inside the living body by moving the plate electrode due to a magnetic field/force between the flexible electrode and the plate electrode. In an exemplary embodiment, the electrical pulse generator may be utilized to apply a pulsed electric field between the flexible electrode and the plate electrode. In an exemplary embodiment, the processing unit may include a memory having processor-readable instructions stored therein and a processor. In an exemplary embodiment, the processor may access the memory and execute the processor-readable instructions. In an exemplary embodiment, the processor may be utilized to perform a method when the processor-readable instructions are executed by the processor. In an exemplary embodiment, the method may include inducing electroporation to the plurality of target cells by applying at least one sequence of electric voltage pulses between the flexible electrode and the plate electrode utilizing the electrical pulse generator.

In an exemplary embodiment, each spherical magnet of the plurality of spherical magnets may include a spherical magnet with a diameter in a range of 0.5 cm to 2 cm. In an exemplary embodiment, the plate electrode may include a plate with a surface area in a range of 10 $cm^2$ to 30 $cm^2$ and a thickness in a range of 2 mm to 5 mm.

In an exemplary embodiment, the plate electrode may be located outside of the target region. In an exemplary embodiment, the plate electrode may be located over skin of the living body or inside the living body within a distance of less than 5 cm from the target region. In an exemplary embodiment, a distance between the plate electrode and the flexible electrode may be within a range of 0.5 mm to 5 cm. In an exemplary embodiment, the flexible electrode may be put inside the target region. In an exemplary embodiment, the flexible electrode may be located inside at least one of intestine, esophagus, vagina, stomach, duodenum, colon, cervix, uterus, and combinations thereof.

In an exemplary embodiment, the system for in-vivo electroporation of the plurality of target cells in the target region of the living body may further include a camera attached to a first spherical magnet of the string of the plurality of spherical magnets. In an exemplary embodiment, the camera may be electrically connected to the processing unit. In an exemplary embodiment, the camera may be utilized to at least one of capture an image from the target region, record a video from the target region, and combinations thereof. In an exemplary embodiment, the method may further include tracking a location of the flexible electrode by at least one of capturing an image from the target region, recording a video from the target region, and combinations thereof utilizing the camera. In an exemplary embodiment, the tracked location of the flexible electrode may be used for placing the flexible electrode at a target location by moving the plate electrode.

In an exemplary embodiment, applying the at least one sequence of electric voltage pulses between the flexible electrode and the plate electrode may include applying at least one sequence of eight square-wave electric voltage pulses with a magnitude in a range of 500 V/cm to 1500 V/cm and a duration of 100 μs between the flexible electrode and the plate electrode.

In an exemplary embodiment, the system for in-vivo electroporation of the plurality of target cells in the target region of the living body may further include two electrically conductive lines. In an exemplary embodiment, the two electrically conductive lines may include a first electrically conductive line and a second electrically conductive line. In an exemplary embodiment, the first electrically conductive line may include a first distal end and a first proximal end. In an exemplary embodiment, the first distal end may be connected to a last spherical magnet of the string of the plurality of spherical magnets and the first proximal end may be connected to a first pole of the electrical pulse generator. In an exemplary embodiment, the second electrically conductive line may include a second distal end and a second proximal end. In an exemplary embodiment, the second distal end may be connected to the plate electrode and the first proximal end may be connected to a second pole of the electrical pulse generator.

BRIEF DESCRIPTION OF THE DRAWINGS

The drawing figures depict one or more implementations in accord with the present teachings, by way of example only, not by way of limitation. In the figures, like reference numerals refer to the same or similar elements.

DESCRIPTION OF EMBODIMENTS

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

Herein, methods, systems, and devices are disclosed for electroporation of target cells, particularly cells of a patient's tissues. In an exemplary embodiment, methods and devices may be utilized for target cells' ablation (e.g., tumor cells destruction) and/or delivery of a substance (e.g., a drug, a diagnostic agent, a therapeutic agent, etc.) to exemplary target cells. In an exemplary embodiment, an exemplary device (e.g., a probe) may be disclosed for target cell's electroporation having one or more electrodes designed based on a location and accessibility of target cells and specific properties of exemplary target cells. In an exemplary embodiment, electrodes of an exemplary device may be designed based on sensitivity of target cells and surrounding areas to an electric field applied during an exemplary electroporation process. In an exemplary embodiment, electrodes of an exemplary probe may be non-invasive electrodes while needle electrodes of conventional electroporation devices may be invasive and unsuitable for all parts of a patient's body.

In one general embodiment of the present disclosure, a probe with wire-blade electrodes is disclosed. In an exemplary embodiment, an exemplary probe may be utilized for non-invasive electroporation of target cells. As used herein, "target cells" may refer to cells of a part of a person's body to be treated by an electrical stimulation (e.g., electroporation); allowing for treatment of exemplary cells including ablating exemplary cells and/or delivery of specific substances (e.g., a drug, a diagnostic agent, a therapeutic agent, etc.) to exemplary cells. In an exemplary embodiment, an exemplary probe may be utilized for superficial electroporation of target cells located near skin and/or in cases where an electrical stimulation in depth may not be allowed. In an exemplary embodiment, an exemplary probe may be utilized for electroporation of target cells in at least one of superficial zones of a tissue or an organ, near-skin tissues or organs, margin zones of a tissue or an organ, and combinations thereof. In an exemplary embodiment, an exemplary probe may be utilized for electroporation of target cells which may not be allowed to inserting a needle therein. In an exemplary embodiment, an exemplary probe may be utilized for electroporation of target cells where inserting a needle there may be harmful.

Figure 1A:
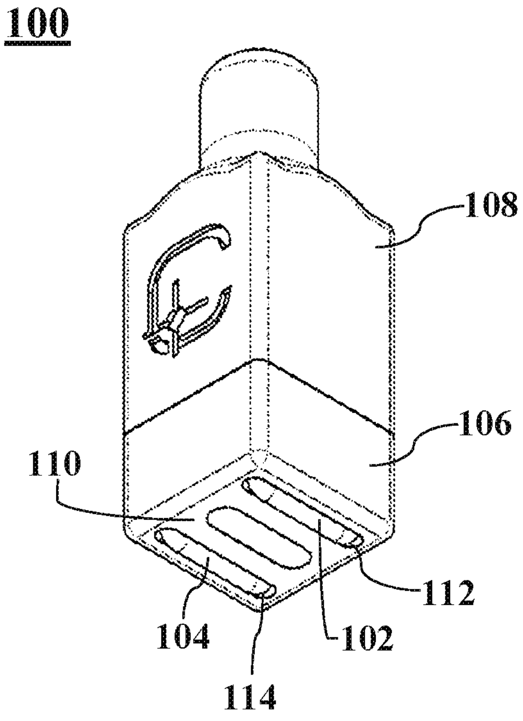
FIG. 1A shows a perspective view of an exemplary vacuum-assisted superficial electroporation probe, consistent with one or more exemplary embodiments of the present disclosure.

FIGS. 1A-1D show different views of a vacuum-assisted superficial electroporation probe 100, consistent with one or more exemplary embodiments of the present disclosure. FIG. 1A shows a perspective view of vacuum-assisted superficial electroporation probe 100, consistent with one or more exemplary embodiments of the present disclosure. In an exemplary embodiment, vacuum-assisted superficial electroporation probe 100 may include two wire blades 102 and 104 mounted on an electrode mounting support 106. In an exemplary embodiment, vacuum-assisted superficial electroporation probe 100 may further include a cap 108 that may be fixed on top of electrode mounting support 106.

In an exemplary embodiment, electrode mounting support 106 may include an enclosed container. In an exemplary embodiment, electrode mounting support 106 may include a hollow container with a circular cross-section, elliptical cross-section, rectangular cross-section, or other geometries. In an exemplary embodiment, electrode mounting support 106 may include a bottom side 110. In an exemplary embodiment, vacuum-assisted superficial electroporation probe 100 may include more than two wire blades similar to wire blades 102 and 104. In an exemplary embodiment, exemplary wire blades may be in parallel relation to each other. In an exemplary embodiment, bottom side 110 may include a plurality of apertures receiving exemplary two or more wire blades, such as wire blades 102 and 104. In an exemplary embodiment, bottom side 110 may include two apertures 112 and 114 receiving wire blades 102 and 104 passing there through. In an exemplary embodiment, wire blades 102 and 104 may be protruded out from respective apertures 112 and 114 of bottom side 110 of electrode mounting support 106.

Figure 1B:
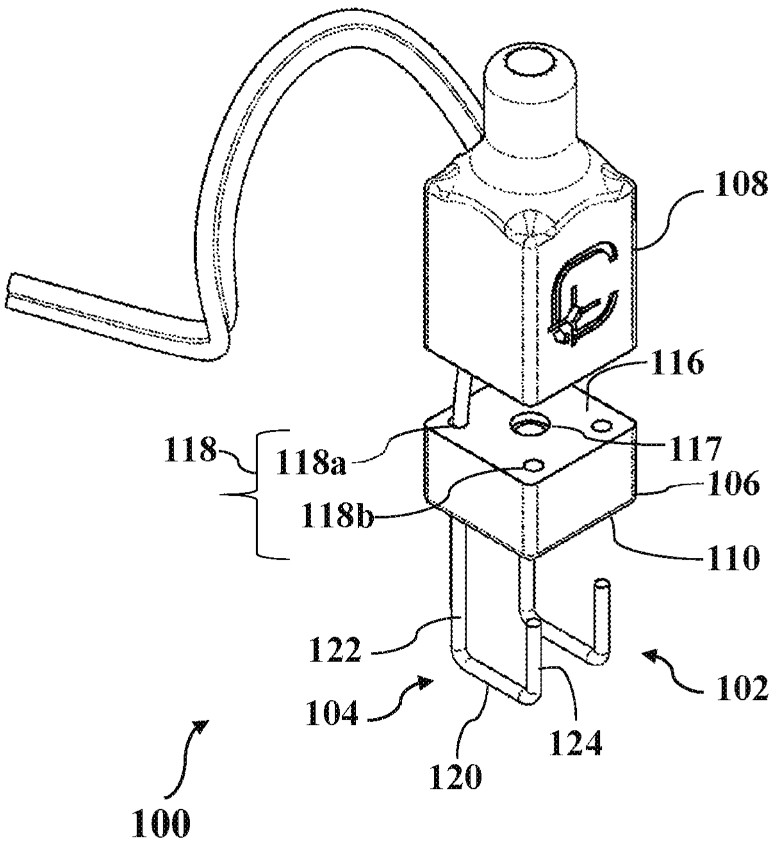
FIG. 1B shows a first exploded perspective view of an exemplary vacuum-assisted superficial electroporation probe, consistent with one or more exemplary embodiments of the present disclosure.
Figure 1C:
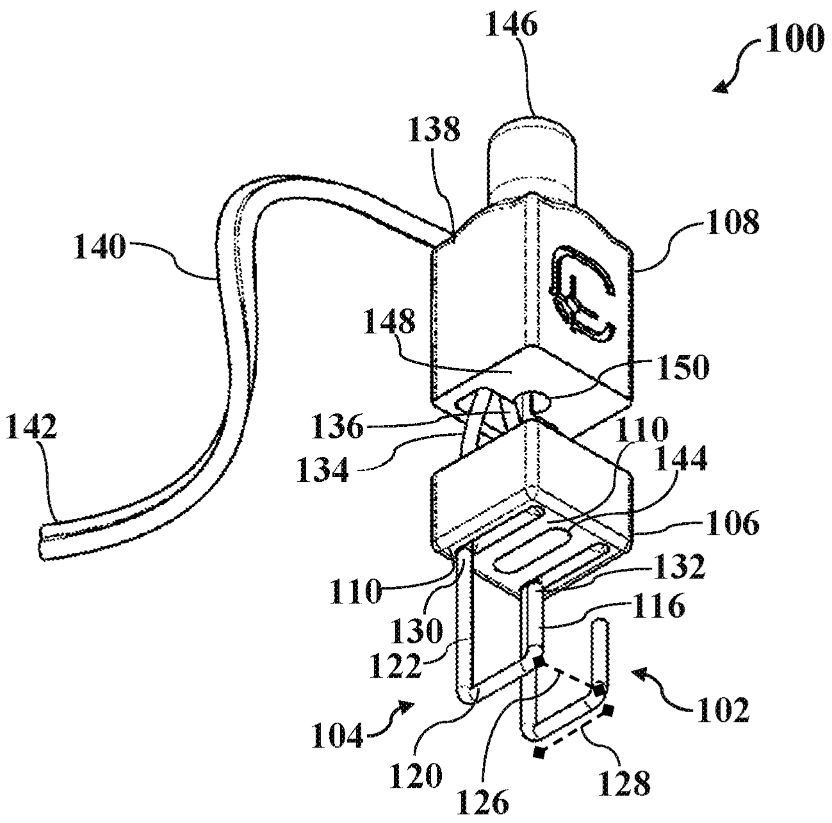
FIG. 1C shows a second exploded perspective view of an exemplary vacuum-assisted superficial electroporation probe, consistent with one or more exemplary embodiments of the present disclosure.

FIGS. 1B-1C show two exploded perspective views of vacuum-assisted superficial electroporation probe 100, consistent with one or more exemplary embodiments of the present disclosure. In an exemplary embodiment, electrode mounting support 106 may include a top side 116. In an exemplary embodiment, top side 116 may include a plurality of pairs of holes 118. In an exemplary embodiment, each pair of holes 118 may receive one wire blade 104 (or 102) passing there through. In an exemplary embodiment, exemplary wire blade 104 may include a U-shaped wire. In an exemplary embodiment, an exemplary U-shaped wire may include a biocompatible electrically conductive wire with a diameter in a range of about 0.5 mm to about 3 mm. In an exemplary embodiment, an exemplary U-shaped wire may be made of steel. In an exemplary embodiment, an exemplary U-shaped wire may be made of medical grade stainless steel. In an exemplary embodiment, exemplary wire blade 104 may include a flat base 120 with two parallel lateral edges 122 and 124 extending upwards from flat base 120. In an exemplary embodiment, a first lateral edge 122 may pass through a first hole 118*a* of pair of holes 118 and a second lateral edge 124 may pass through a second hole 118*b* of pair of holes 118. In an exemplary embodiment, a hollow path for passing exemplary wire blade 104 there through may be defined by pair of holes 118 embedded in top side 116 and aperture 114 embedded in bottom side 110. In an exemplary embodiment, pair of holes 118 may be aligned to aperture 114 so that pair of holes 118 may be along aperture 114. In an exemplary embodiment, flat base 120 may pass through aperture 114 and protrude out from aperture 114; allowing for putting flat base 120 in contact with a zone of a tissue of a living body including a plurality of target cells.

Referring to FIG. 1C, wire blades 102 and 104 may be in parallel relation to each other with a distance 126 in a range of about 0.5 cm to about 1.5 cm from each other. In an exemplary embodiment, flat base 120 of each wire blade 104 may have a length 128 in a range of about 0.5 cm to about 1.5 cm. In an exemplary embodiment, a length in a range of about 0.1 mm to about 0.5 mm of each lateral edge 122 or 124 may be protruded out from bottom side 110 of electrode mounting support 106.

In an exemplary embodiment, referring to FIGS. 1B-1C, each wire blade 104 may include two free ends 130 and 132. In an exemplary embodiment, a first free end 130 may be connected to an electrically conductive wire 134. In an exemplary embodiment, first free end 130 may be welded to electrically conductive wire 134. Similarly, a connection may be formed between wire blade 102 and an electrically conductive wire 136. In an exemplary embodiment, second free end 132 may exit from second hole **118*b* and may be fixed onto top side 116 of electrode mounting support 106**.

In an exemplary embodiment, wire blades 102 and 104 may be utilized for transferring (applying) an electrical signal (e.g., a pulsed electric field) to a plurality of target cells to be treated via electrical stimulation (e.g., electroporation). So, an electrical connection between wire blades 102 and 104 and an electrical power supply (e.g., an electrical pulse generator) may be formed via electrically conductive wires 134 and 136. In an exemplary embodiment, electrically conductive wires 134 and 136 may pass through a first outlet 138 of cap 108 and connect to an exemplary power supply. In an exemplary embodiment, electrically conductive wires 134 and 136 may be put inside a connecting line 140 and an end 142 of connecting line 140 including two respective ends of electrically conductive wires 134 and 136 may be connected to an exemplary power supply.

In an exemplary embodiment, wire blades 102 and 104 may be put in superficial contact with at least one of a tissue, an organ, or a portion thereof in the vicinity of a plurality of target cells. In an exemplary embodiment, wire blades 102 and 104 may be put in contact with a zone of at least one of a tissue, an organ, or a portion thereof including a plurality of target cells. In an exemplary embodiment, an electric potential may be applied to wire blades 102 and 104 so that an exemplary electric field may be generated in an area including an exemplary plurality of target cells. In an exemplary embodiment, a pulsed electric field may be applied between wire blades 102 and 104 and an exemplary pulsed electric field may be generated inside an exemplary zone including an exemplary plurality of target cells. In an exemplary embodiment, an exemplary plurality of target cells of at least one of an exemplary tissue, an exemplary organ, or an exemplary portion thereof may be affected by an exemplary electric field applied between wire blades 102 and 104. In an exemplary embodiment, an exemplary plurality of target cells may be electroporated due to an exemplary electric field applied between wire blades 102 and 104.

In an exemplary embodiment, an exemplary zone of at least one of a tissue, an organ, or a portion thereof including an exemplary plurality of target cells may be scanned by moving wire blades 102 and 104 all over an exemplary zone and applying an exemplary electric field; thereby, resulting in electrically stimulating (e.g., electroporating) of all exemplary plurality of target cells. In an exemplary embodiment, a contact between wire blades 102 and 104 and an exemplary zone including an exemplary plurality of target cells may not need an insertion of wire blades 102 and 104 into an exemplary zone and a superficial contact between wire blades 102 and 104 and an exemplary zone may be enough for generating an exemplary electric field in an exemplary zone and electrically affecting exemplary plurality of target cells so that a non-invasive contact between wire blades 102 and 104 and an exemplary zone and a non-invasive electrically stimulation of an exemplary plurality of target cells may be achieved. In an exemplary embodiment, wire blades 102 and 104 may be put over skin at a location adjacent to an exemplary zone. In another exemplary embodiment, wire blades 102 and 104 may be put inside a person's body at a location adjacent to an exemplary zone while a direct access to an exemplary zone being provided during a surgery.

Figure 1D:
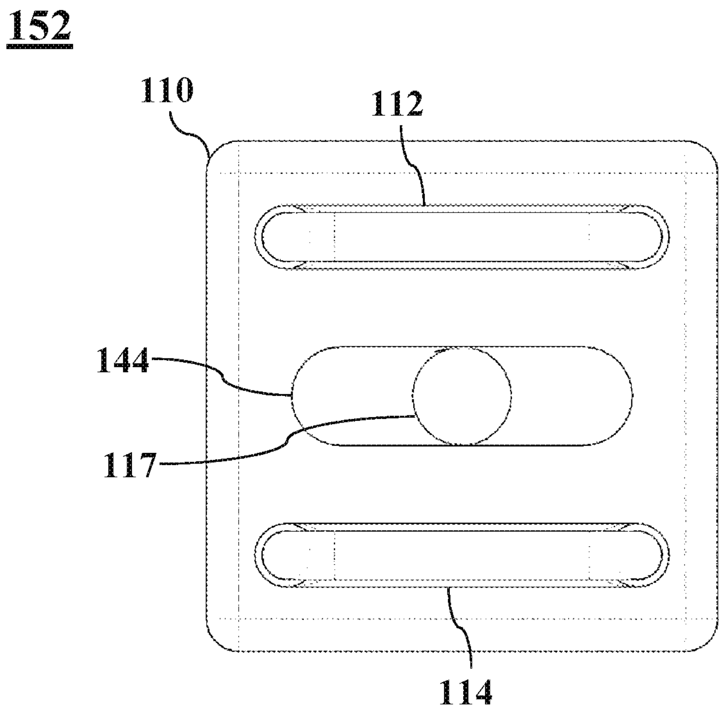
FIG. 1D shows a bottom view of an exemplary vacuum-assisted superficial electroporation probe, consistent with one or more exemplary embodiments of the present disclosure.

In an exemplary embodiment, vacuum-assisted superficial electroporation probe 100 may further include a path for applying a vacuum pressure onto at least one of an exemplary tissue, an exemplary organ, or an exemplary portion thereof within an area in the vicinity of an exemplary target cells; allowing for forming a firm and complete contact between at least one of an exemplary tissue, an exemplary organ, or an exemplary portion thereof and wire blades 102 and 104. In an exemplary embodiment, an exemplary path for applying an exemplary vacuum pressure may include an open path along a height of vacuum-assisted superficial electroporation probe 100 from bottom side 110 to top of cap 108. In an exemplary embodiment, an exemplary path for applying an exemplary vacuum pressure may include a hollow path extending from bottom side 110 to top of cap 108 including hollow spaces of each aperture 114 and respective pair of holes 118 around each wire blade 104. In another exemplary embodiment, an exemplary path for applying an exemplary vacuum pressure may be designed by embedding openings in bottom side 110 and top side 116 aligned to each other along an exemplary height of vacuum-assisted superficial electroporation probe 100. In an exemplary embodiment, an exemplary path for applying an exemplary vacuum pressure may be isolated from hollow spaces of each aperture 114 and respective pair of holes 118 around each wire blade 104 to avoid perturbation of electrical properties of a medium between two wire blades 102 and 104. In an exemplary embodiment, referring to FIG. 1B, top side 116 may further include a singular hole 117 and bottom side 110 may further include an aperture 144 (illustrated in FIG. 1C) defining an exemplary hollow path extending along electrode mounting support 106; allowing for applying an exemplary vacuum pressure there through. In an exemplary embodiment, singular hole 117 may be located at a center of top side 116 of electrode mounting support 106. In an exemplary embodiment, aperture 144 may be located at a center of bottom side 110 along with singular hole 117. In an exemplary embodiment, an exemplary hollow path may extend from bottom side 110 continuing to a second outlet 146 of cap 108 where a first end of a vacuum tube may be received and attached thereon. In an exemplary embodiment, a second end of an exemplary vacuum tube may be connected to a vacuum pressure generator. Referring to FIG. 1C, cap 108 may include a bottom surface 148 including an opening 150. In an exemplary embodiment, opening 150 may be located along with an exemplary hollow path of applying an exemplary vacuum pressure there through. In an exemplary embodiment, opening 150 may be located along with second outlet 146 of cap 106. In an exemplary embodiment, opening 150 may receive electrically conductive wires 134 and 136 passing there through. Moreover, FIG. 1D shows a bottom view 152 of vacuum-assisted superficial electroporation probe 100, consistent with one or more exemplary embodiments of the present disclosure. An arrangement of singular hole 117, aperture 144, and two apertures 112 and 114 may be seen in FIG. 1D.

Figure 1E:
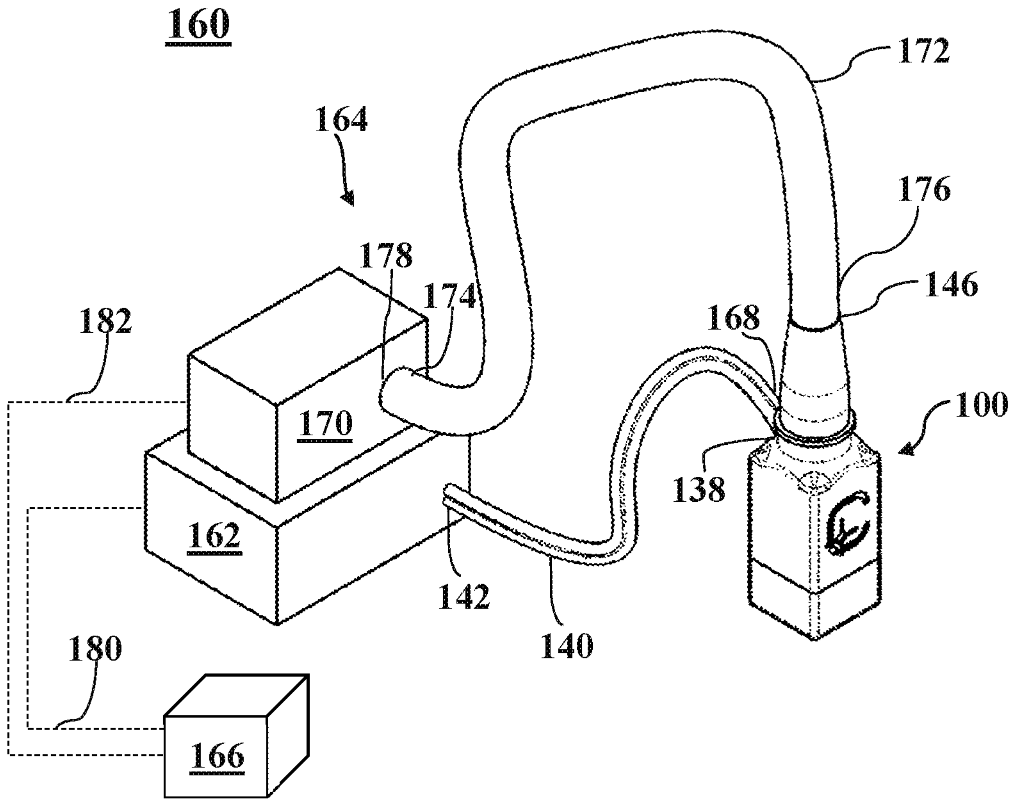
FIG. 1E shows an exemplary system for superficial electroporation, consistent with one or more exemplary embodiments of the present disclosure.

In an exemplary embodiment, vacuum-assisted superficial electroporation probe 100 may be utilized for applying a therapeutic method via electrical stimulation (e.g., electroporation) of cells of a living body, for example, tumor cells of a cancer patient. In an exemplary embodiment, a system for superficial electroporation including vacuum-assisted superficial electroporation probe 100 may be disclosed. FIG. 1E shows a system 160 for superficial electroporation, consistent with one or more exemplary embodiments of the present disclosure. In an exemplary embodiment, system 160 may include vacuum-assisted superficial electroporation probe 100, an electrical pulse generator 162, a vacuum device 164, and a processing unit 166.

In an exemplary embodiment, electrical pulse generator 162 may be electrically connected to vacuum-assisted superficial electroporation probe 100 via connecting line 140. In an exemplary embodiment, electrical pulse generator 162 may be an example of an exemplary power supply. In an exemplary embodiment, electrical pulse generator 162 may include an electroporation pulse generator. In an exemplary embodiment, electrical pulse generator 162 may be electrically connected to wire blades 102 and 104 of vacuum-assisted superficial electroporation probe 100 via connecting line 140. In an exemplary embodiment, connecting line 140 may contain electrically conductive wires 134 and 136 respectively connected to wire blades 102 and 104 of vacuum-assisted superficial electroporation probe 100. In an exemplary embodiment, a first end 168 of connecting line 140 may pass through a first outlet 138 of cap 108 and a second end 142 of connecting line 140 may be connected to electrical pulse generator 162. In an exemplary embodiment, electrical pulse generator 162 may be utilized to apply electrical pulses to wire blades 102 and 104 while wire blades 102 and 104 being put in contact with an exemplary zone in a living body including an exemplary plurality of target cells; thereby, resulting in generating a pulsed electric field within an exemplary zone stimulating an exemplary plurality of target cells.

In an exemplary embodiment, vacuum device 164 may include a vacuum pressure generator 170 and a vacuum tube 172. In an exemplary embodiment, vacuum device 164 may be utilized to apply a vacuum pressure to an exemplary zone in an exemplary living body including an exemplary plurality of target cells while wire blades 102 and 104 being put in contact with an exemplary zone; thereby, forming a firm contact between wire blades 102 and 104 and an exemplary zone. In an exemplary embodiment, an exemplary firm contact between wire blades 102 and 104 and an exemplary zone may allow for generating a uniform and strong pulsed electric field inside an exemplary zone with high yield of electrical effect on an exemplary plurality of target cells. In an exemplary embodiment, a firm contact between wire blades 102 and 104 and an exemplary zone may maximize a penetration depth of an exemplary generated pulsed electric field; and therefore, elevate efficiency of therapy. In an exemplary embodiment, vacuum tube 172 may include a flexible tube. In an exemplary embodiment, vacuum tube 172 may include a flexible polymer-based tube which may be able to be medically sterilized. In an exemplary embodiment, vacuum tube 172 may include a tube made of silicon. In an exemplary embodiment, vacuum pressure generator 170 may be connected to vacuum-assisted superficial electroporation probe 100 via vacuum tube 172. In an exemplary embodiment, vacuum tube 172 may include a proximal end 174 and a distal end 176. In an exemplary embodiment, proximal end 174 may be attached and fixed onto an outlet 178 of vacuum pressure generator 170. In an exemplary embodiment, distal end 176 may be fixed at a location on top of an exemplary hollow path along vacuum-assisted superficial electroporation probe 100 for applying an exemplary vacuum pressure there through. In an exemplary embodiment, distal end 176 may be fixed at second outlet 146 of cap 108. In an exemplary embodiment, vacuum pressure generator 170 may be utilized to apply a suction pressure to an area at the bottom of vacuum-assisted superficial electroporation probe 100 through vacuum tube 172 and an exemplary hollow path along vacuum-assisted superficial electroporation probe 100. In an exemplary embodiment, vacuum tube 172 may transfer an exemplary suction pressure to an exemplary plurality of target cells while flat base 120 of exemplary wire blade 104 (and similarly, an exemplary flat base of wire blade 102) may be in contact with an exemplary zone of an exemplary tissue of an exemplary living body including an exemplary plurality of target cells. In an exemplary embodiment, an exemplary applied suction pressure may gently pull an exemplary zone of an exemplary tissue towards wire blades 102 and 104; thereby, resulting in a firm contact between wire blades 102 and 104 and an exemplary zone of an exemplary tissue.

Referring to FIG. 1E, processing unit 166 may be electrically connected to electrical pulse generator 162 and vacuum pressure generator 170 via a wireless connection or utilizing respective electrically conductive wires 180 and 182. In an exemplary embodiment, processing unit 166 may include a memory having processor-readable instructions stored therein and a processor. In an exemplary embodiment, an exemplary processor may be utilized to access an exemplary memory and execute exemplary processor-readable instructions. In an exemplary embodiment, executing exemplary processor-readable instructions by an exemplary processor may configure an exemplary processor to perform a method. In an exemplary embodiment, an exemplary method may include applying a therapeutical treatment to an exemplary plurality of target cells inside an exemplary living body by electrically stimulating an exemplary plurality of target cells. In an exemplary embodiment, an exemplary method may include at least one of treating an exemplary plurality of target cells, ablating an exemplary plurality of target cells, delivering a drug or therapeutical substance to an exemplary plurality of target cells, and combinations thereof by electroporation an exemplary plurality of target cells.

Figure 2:
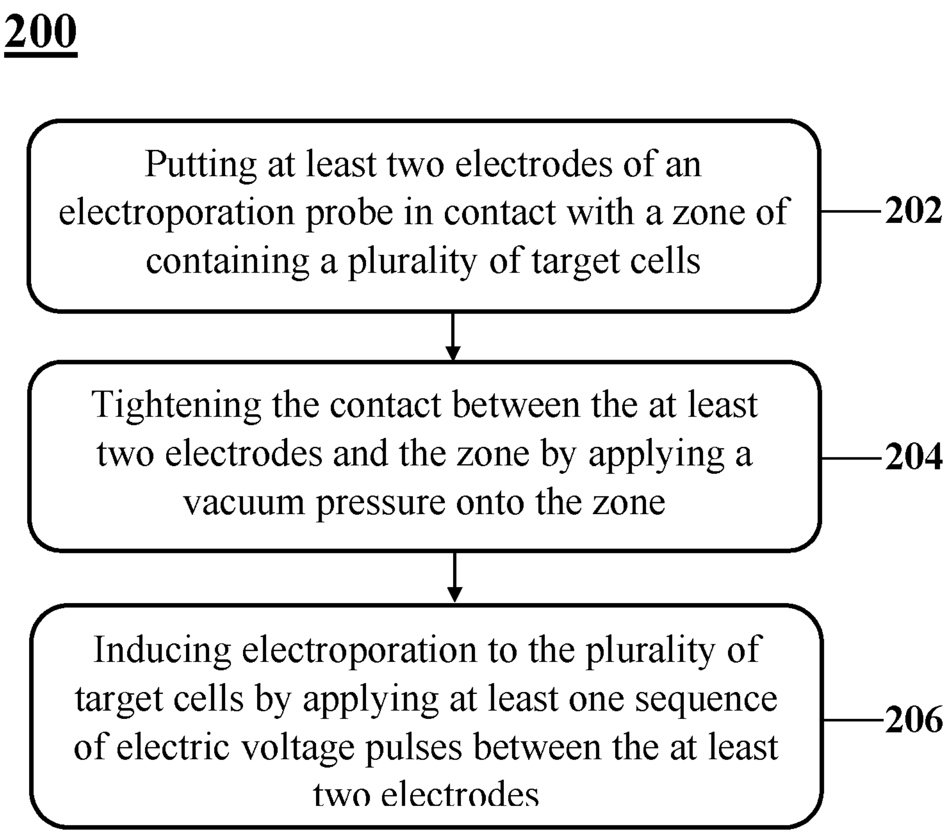
FIG. 2 shows an exemplary method for superficial electroporation of an exemplary plurality of target cells, consistent with one or more exemplary embodiments of the present disclosure.

FIG. 2 shows a method 200 for superficial electroporation of an exemplary plurality of target cells, consistent with one or more exemplary embodiments of the present disclosure. In an exemplary embodiment, method 200 may include putting at least two electrodes of an electroporation probe in contact with a zone of a living body containing an exemplary plurality of target cells (step 202), tightening a contact between at least two exemplary electrodes and an exemplary zone by pulling an exemplary zone towards at least two exemplary electrodes via applying a vacuum pressure onto an exemplary zone (step 204), and inducing electroporation to an exemplary plurality of target cells by applying at least one sequence of electric voltage pulses between at least two exemplary electrodes (step 206). In an exemplary embodiment, method 200 may be carried out utilizing vacuum-assisted superficial electroporation probe 100 and system 160. So, method 200 may be described herein below in connection with FIGS. 1A-1E.

In further detail with respect to step 202, at least two electrodes of electroporation probe 100 may be put in contact with an exemplary zone of an exemplary living body, where an exemplary zone may contain an exemplary plurality of target cells. In an exemplary embodiment, putting at least two electrodes of electroporation probe 100 in contact with an exemplary zone of an exemplary living body may include putting wire blades 102 and 104 in contact with at least one of a superficial zone of a tissue or an organ, a zone of a near-skin tissue or an organ, a margin zone of a tissue or an organ, and combinations thereof. In an exemplary embodiment, wire blades 102 and 104 may be put in contact with remaining parts or margins of a dissected tumor. In an exemplary embodiment, wire blades 102 and 104 may be put in contact with surface of inner walls of abdomen, breast tissue, surfaces of the intestines, bladder and vessels that may be suspected to be cancerous. In an exemplary embodiment, wire blades 102 and 104 may be put in contact with an exemplary zone including an exemplary plurality of target cells by putting wire blades 102 and 104 inside an exemplary zone to a depth of less than about 5 mm. In an exemplary embodiment, wire blades 102 and 104 may be put in contact with an exemplary zone by putting wire blades 102 and 104 inside an exemplary zone to a depth in a range of about 3 mm to about 5 mm.

In an exemplary embodiment, in many cases of sarcoma, remnants of a dissected tumor in an inner wall of abdomen and pelvis, surface of large intestine and small intestine, and involved vessels' walls, and not completely cleared zones of a tumor tissue may be completely treated utilizing method 200 and system 160. In an exemplary embodiment, wire blades 102 and 104 may with a firm connection to surfaces of an exemplary tissue or organ may be used for electro-chemotherapy of an exemplary tissue or organ without causing any damage or bleeding in an exemplary site. In an exemplary embodiment, putting wire blades 102 and 104 inside an exemplary zone may include non-invasive insertion of wire blades 102 and 104 inside an exemplary zone, whereas a common electroporation of an exemplary zone utilizing common devices and systems requires invasive insertion of at least one needle into an exemplary zone. As another example, applying any electrical stimulation in spinal column faces challenges due to high density of nerves in this area. In an exemplary embodiment, wire blades 102 and 104 may be utilized with a capability of a non-invasive superficial electrical contact with an exemplary zone in spinal column. In general, a structure of wire blades 102 and 104 may be appropriate for all cases where an electrical stimulation in depth is not allowed.

In further detail with respect to step 204, step 204 may include tightening a contact between at least two exemplary electrodes and an exemplary zone by pulling an exemplary zone towards at least two exemplary electrodes via applying a vacuum pressure onto an exemplary zone. In an exemplary embodiment, tightening an exemplary contact between at least two exemplary electrodes and an exemplary zone may include forming a firm electrically conductive connection between wire blades 102 and 104 and an exemplary zone containing an exemplary plurality of target cells. In an exemplary embodiment, a firm contact may be formed between respective flat bases of wire blades 102 and 104 and an exemplary zone by pulling an exemplary zone towards wire blades 102 and 104 via applying an exemplary vacuum pressure onto an exemplary zone. In an exemplary embodiment, pulling an exemplary zone towards wire blades 102 and 104 may include applying an exemplary vacuum pressure through an exemplary hollow path along vacuum-assisted superficial electroporation probe 100 utilizing vacuum device 164. In an exemplary embodiment, applying an exemplary vacuum pressure onto an exemplary zone may include applying a vacuum pressure with a magnitude in a range of about −0.5 bar to −0.7 bar at proximal end 174 of vacuum tube 172 utilizing vacuum pressure generator 170. In an exemplary embodiment, a vacuum pressure of about −0.7 bar may be applied onto an exemplary zone.

In further detail with respect to step 206, step 206 may include inducing electroporation to an exemplary plurality of target cells by applying at least one sequence of electric voltage pulses between wire blades 102 and 104. In an exemplary embodiment, applying at least one sequence of electric voltage pulses between wire blades 102 and 104 may include applying at least one sequence of eight square-wave electric voltage pulses with a magnitude in a range of about 500 V/cm to about 1500 V/cm and a duration of about 100 μs.

In an exemplary embodiment, method 200 may further include a step of injecting a drug or a therapeutical substance from a reservoir of electroporation probe 100 or using an injection syringe into a location in the vicinity of an exemplary zone containing an exemplary plurality of cells. In an exemplary embodiment, an exemplary injected drug or therapeutical substance may penetrate into electroporated exemplary plurality of target cells; thereby, resulting in treating an exemplary plurality of target cells.

Figure 3A:
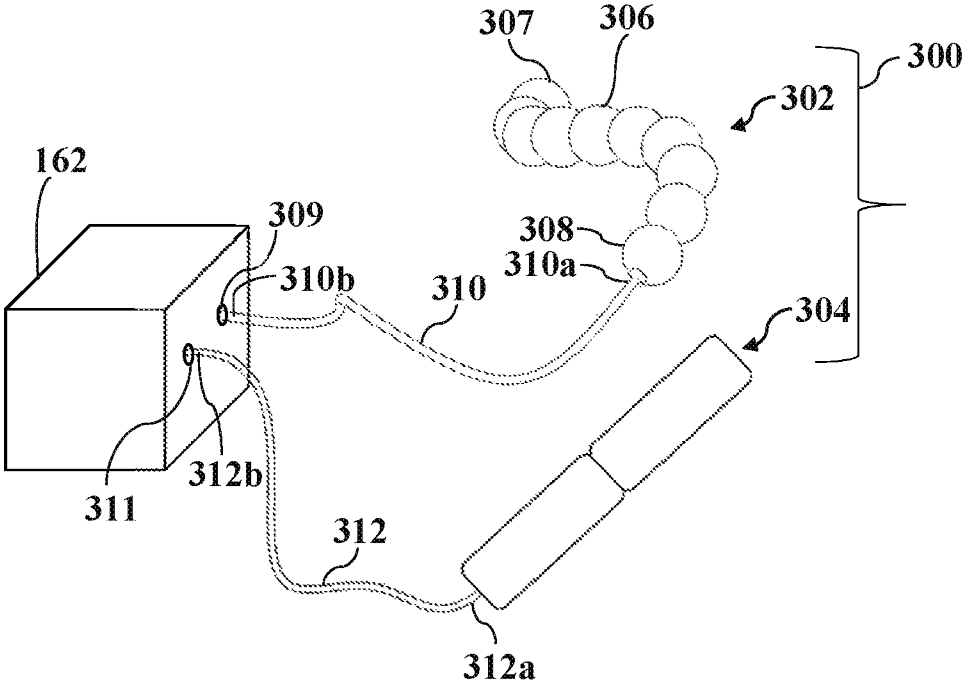
FIG. 3A shows a view of an exemplary electroporation device connected to an exemplary electrical pulse generator, consistent with one or more exemplary embodiments of the present disclosure.

In another general aspect of the present disclosure, an electroporation device for in-vivo electroporation of a plurality of target cells may be disclosed. In an exemplary embodiment, an exemplary electroporation device may be utilized for electroporation of target cells in a lumen-shaped or a cavity-shaped part of a living body. FIG. 3A shows a view of electroporation device 300 connected to electrical pulse generator 162, consistent with one or more exemplary embodiments of the present disclosure. In an exemplary embodiment, electroporation device 300 may be utilized for transferring a pulsed electric field generated by electrical pulse generator 162 to an exemplary plurality of target cells. In an exemplary embodiment, an exemplary plurality of target cells may be in an exemplary lumen-shaped or cavity-shaped part of an exemplary living body.

Referring to a FIG. 3A, electroporation device 300 may include a flexible electrode 302 and a plate electrode 304. In an exemplary embodiment, flexible electrode 302 may include a string of a plurality of spherical magnets 306 connected in series. In an exemplary embodiment, flexible electrode 302 may have a variable length. In an exemplary embodiment, length of flexible electrode 302 may be adjustable by adding or removing one or more spherical magnets 306. In an exemplary embodiment, flexible electrode 302 may be put inside an exemplary living body. In an exemplary embodiment, flexible electrode 302 may be put in the vicinity of a target region containing an exemplary plurality of target cells inside an exemplary living body. In an exemplary embodiment, an exemplary target region may include at least one of intestine, esophagus, vagina, stomach, duodenum, colon, cervix, uterus, and combinations thereof. In an exemplary embodiment, flexible electrode 302 may be put inside at least one of intestine, esophagus, vagina, stomach, duodenum, colon, cervix, uterus, and combinations thereof.

In an exemplary embodiment, each spherical magnet 306 may include a spherical magnet with a diameter in a range of about 0.5 cm to about 2 cm. In an exemplary embodiment, a first spherical magnet 307 may be inserted and placed inside an exemplary target region of an exemplary living body to be electroporated. In an exemplary embodiment, one or more spherical magnets 306 may be added to first spherical magnet 307 to form flexible electrode 302 inside an exemplary target region. In an exemplary embodiment, number of spherical magnets 306 may be determined based on a size of an exemplary target region to be electroporated. In an exemplary embodiment, one or more spherical magnets 306 may be removed from an exemplary string of plurality of spherical magnets 306 while removing flexible electrode 302 from an exemplary target region or when reducing a length of flexible electrode 302 is required.

In an exemplary embodiment, a last spherical magnet 308 of an exemplary string of a plurality of spherical magnets 306 of flexible electrode 302 may be connected to a first pole 309 of electrical pulse generator 162. In an exemplary embodiment, last spherical magnet 306 may be connected to electrical pulse generator 162 via a first electrically conductive line 310. In an exemplary embodiment, first electrically conductive line 310 may include a first distal end 310*a* and a first proximal end 310*b*. In an exemplary embodiment, first distal end 310*a* may be connected to last spherical magnet 308 of an exemplary string of plurality of spherical magnets 306, and first proximal end 310*b* may be connected to first pole 309 of electrical pulse generator 162.

In an exemplary embodiment, plate electrode 304 may include a plate magnet or a ferromagnetic steel plate. In an exemplary embodiment, plate electrode 304 may be put in the vicinity of an exemplary target region. In an exemplary embodiment, plate electrode 304 may include a plate with a surface area in a range of about 10 $cm^2$ to about 30 $cm^2$. In an exemplary embodiment, plate electrode 304 may include a plate with a thickness in a range of 0.5 mm to 10 mm. In an exemplary embodiment, plate electrode 304 may include a plate with a thickness in a range of 2 mm to 5 mm. In an exemplary embodiment, plate electrode 304 may include a square-shaped plate with dimensions of 5 cm×5 cm.

In an exemplary embodiment, plate electrode 304 may be connected to electrical pulse generator 162 via a second electrically conductive line 312. In an exemplary embodiment, second electrically conductive line 312 may include a second distal end 312*a* and a second proximal end 312*b*. In an exemplary embodiment, second distal end 312*a* may be connected to plate electrode 304, and second proximal end 312*b* may be connected to second pole 311 of electrical pulse generator 162.

In an exemplary embodiment, plate electrode 304 may be placed over skin of an exemplary living body or inside an exemplary living body within a distance of less than about 10 cm from an exemplary target region. In an exemplary embodiment, plate electrode 304 may be located within a distance of less than about 5 cm from an exemplary target region. In an exemplary embodiment, plate electrode 304 may be located within a distance of less than about 10 cm from flexible electrode 302. In an exemplary embodiment, a distance between plate electrode 304 and flexible electrode 302 may be within a range of about 0.5 mm to about 5 cm. In an exemplary embodiment, flexible electrode 302 may be movable inside an exemplary living body by moving plate electrode 304 due to a magnetic field/force between flexible electrode 302 and plate electrode 304. In an exemplary embodiment, flexible electrode 302 may be put in contact with all parts of an exemplary target region by moving plate electrode 304. In an exemplary embodiment, a movement of flexible electrode 302 inside an exemplary target region may be guided by moving plate electrode 304; allowing for applying an electric field inside all parts of an exemplary target region. In an exemplary embodiment, an exemplary electric field may be generated in an exemplary target region between plate electrode 304 and flexible electrode 302 by applying an electric voltage between plate electrode 304 and flexible electrode 302 using electrical pulse generator 162. In an exemplary embodiment, a pulsed electric field may be generated between plate electrode 304 and flexible electrode 302 utilizing electrical pulse generator 162. In an exemplary embodiment, an exemplary generated pulsed electric field may allow for electroporating an exemplary plurality of target cells of an exemplary target region. In an exemplary embodiment, an exemplary plurality of target cells may be ablated due to an exemplary applied pulsed electric field to an exemplary target region. In an exemplary embodiment, an exemplary generated pulsed electric field may be generated by applying at least one sequence of electric voltage pulses between plate electrode 304 and flexible electrode 302 utilizing electrical pulse generator 162. In an exemplary embodiment, applying the at least one sequence of electric voltage pulses between plate electrode 304 and flexible electrode 302 may include applying at least one sequence of eight square-wave electric voltage pulses with a magnitude in a range of 500 V/cm to 1500 V/cm and a duration of 100 μs between plate electrode 304 and flexible electrode 302 using utilizing electrical pulse generator 162.

Figure 3B:
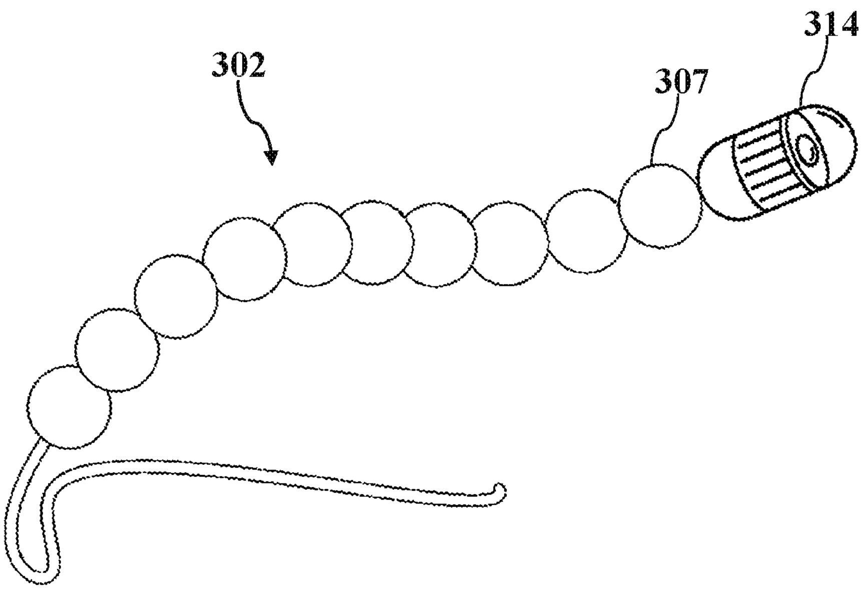
FIG. 3B shows an exemplary flexible electrode and an exemplary camera attached to an exemplary flexible electrode, consistent with one or more exemplary embodiments of the present disclosure.

In an exemplary embodiment, electroporation device 300 may further include a camera attached to flexible electrode 302. FIG. 3B shows flexible electrode 302 and a camera 314 attached to flexible electrode 302, consistent with one or more exemplary embodiments of the present disclosure. In an exemplary embodiment, camera 314 may include a digital camera. In an exemplary embodiment, camera 314 may be utilized for at least one of capturing an image, recording a video, and combinations thereof from a zone where flexible electrode 302 may be placed. In an exemplary embodiment, camera 314 may be connected to a processing unit for recording and processing an exemplary captured image and/or recorded video from an exemplary zone, for example, an exemplary target region. In an exemplary embodiment, camera 314 may be connected to an exemplary processing unit structurally and functionally similar to processing unit 166. In an exemplary embodiment, camera 314 may be connected to an exemplary processing unit via a wireless connection. In an exemplary embodiment, an exemplary captured image and/or recorded video from an exemplary zone may be utilized for tracking a location of flexible electrode 302 or guiding a location of flexible electrode 302 to be adjusted at a target location by moving plate electrode 304. In an exemplary embodiment, camera 314 may be attached to first spherical magnet 307. In an exemplary embodiment, camera 314 may include an endoscope camera.

Figure 3C:
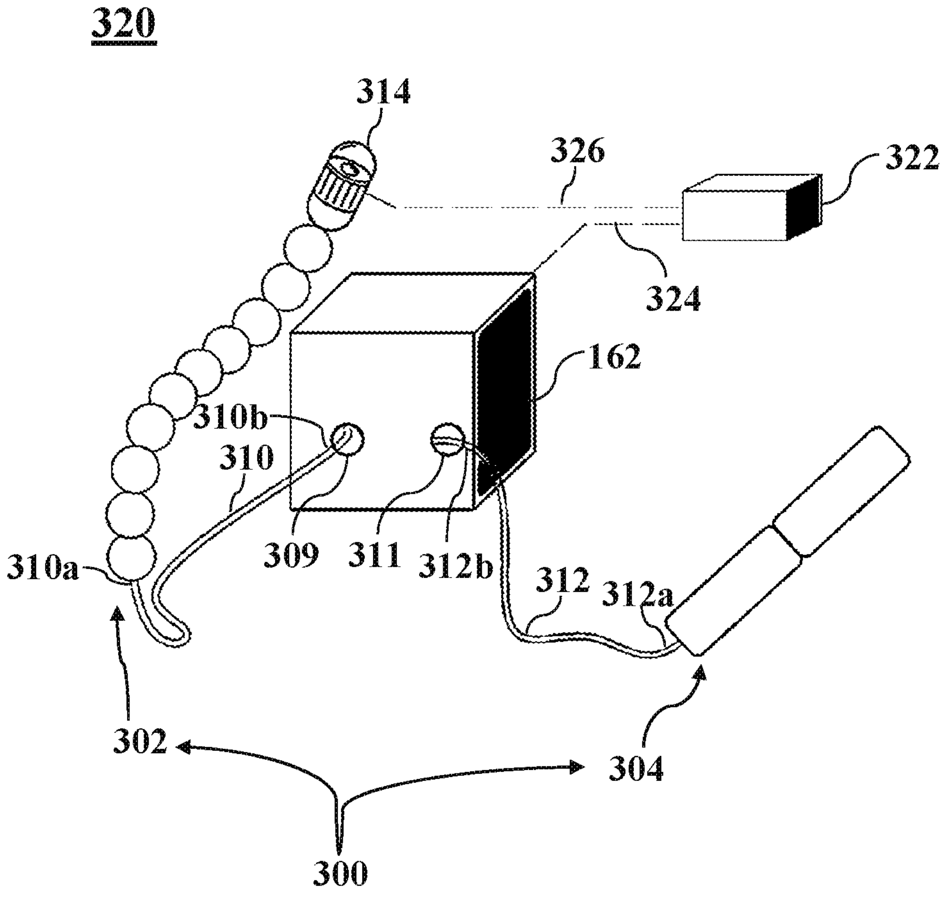
FIG. 3C shows an exemplary system for in-vivo electroporation, consistent with one or more exemplary embodiments of the present disclosure.

In an exemplary embodiment of the present disclosure, a system including electroporation device 300 and electrical pulse generator 162 may be disclosed for in-vivo electroporation of an exemplary plurality of target cells in an exemplary target region of an exemplary living body. FIG. 3C shows a system 320 for in-vivo electroporation, consistent with one or more exemplary embodiments of the present disclosure. In an exemplary embodiment, system 320 may include electroporation device 300, electrical pulse generator 162, and processing unit 322 connected to electrical pulse generator 162 via connection line 324. In an exemplary embodiment, system 320 may further include camera 314 connected to processing unit 322 via connection line 326. In an exemplary embodiment, each of connection lines 324 or 326 may include an electrically conductive line or a wireless connection line including Bluetooth devices or Bluetooth modules embedded in camera 314, electrical pulse generator 162, and processing unit 322.

Referring to FIG. 3C, processing unit 322 may be electrically connected to electrical pulse generator 162 and camera 314 via respective electrically conductive wires or wireless connections 324 and 326. In an exemplary embodiment, processing unit 166 may include a memory having processor-readable instructions stored therein and a processor. In an exemplary embodiment, an exemplary processor may be utilized to access an exemplary memory and execute exemplary processor-readable instructions. In an exemplary embodiment, executing exemplary processor-readable instructions by an exemplary processor may configure an exemplary processor to perform a method. In an exemplary embodiment, an exemplary method may include applying a therapeutical treatment to an exemplary plurality of target cells inside an exemplary living body by electrically stimulating an exemplary plurality of target cells. In an exemplary embodiment, an exemplary method may include at least one of treating an exemplary plurality of target cells, ablating an exemplary plurality of target cells, delivering a drug or therapeutical substance to an exemplary plurality of target cells, and combinations thereof by electroporation an exemplary plurality of target cells.

Figure 4A:
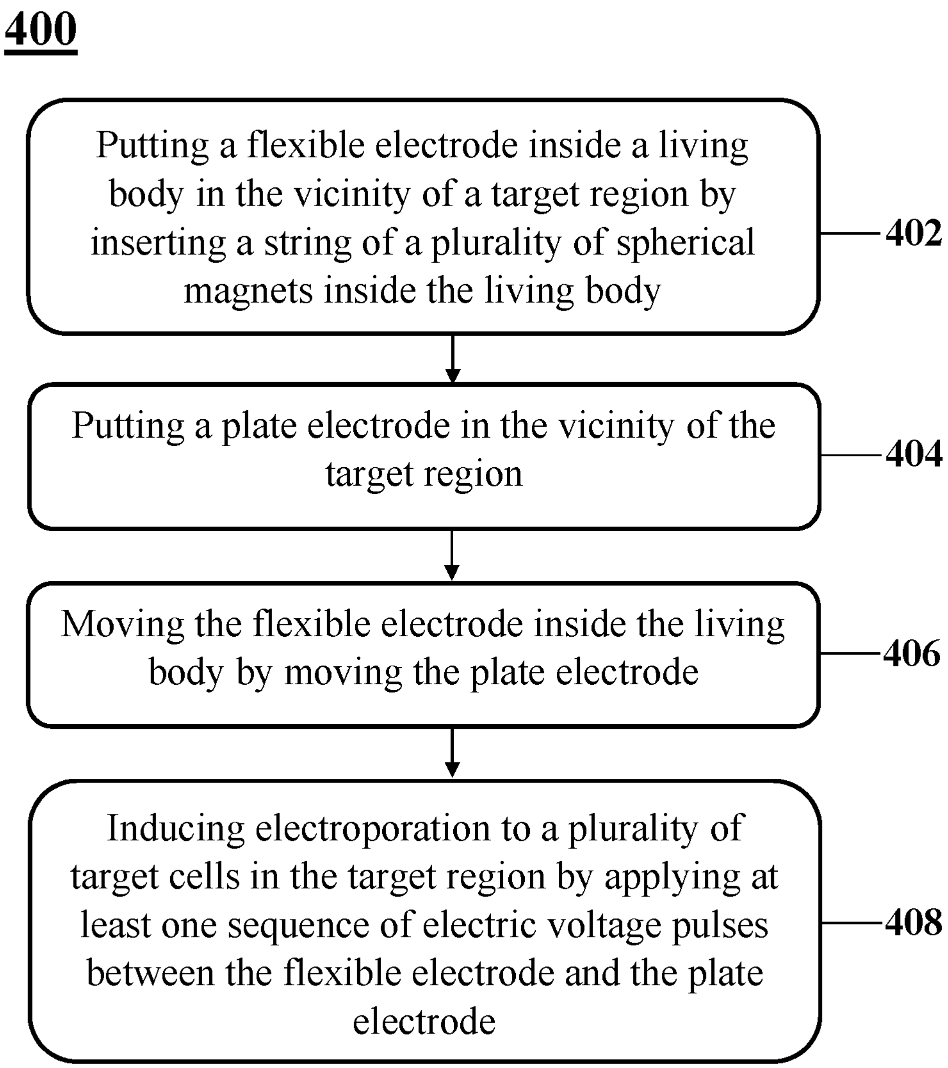
FIG. 4A shows an exemplary method for in-vivo electroporation of an exemplary plurality of target cells, consistent with one or more exemplary embodiments of the present disclosure.
Figure 4B:
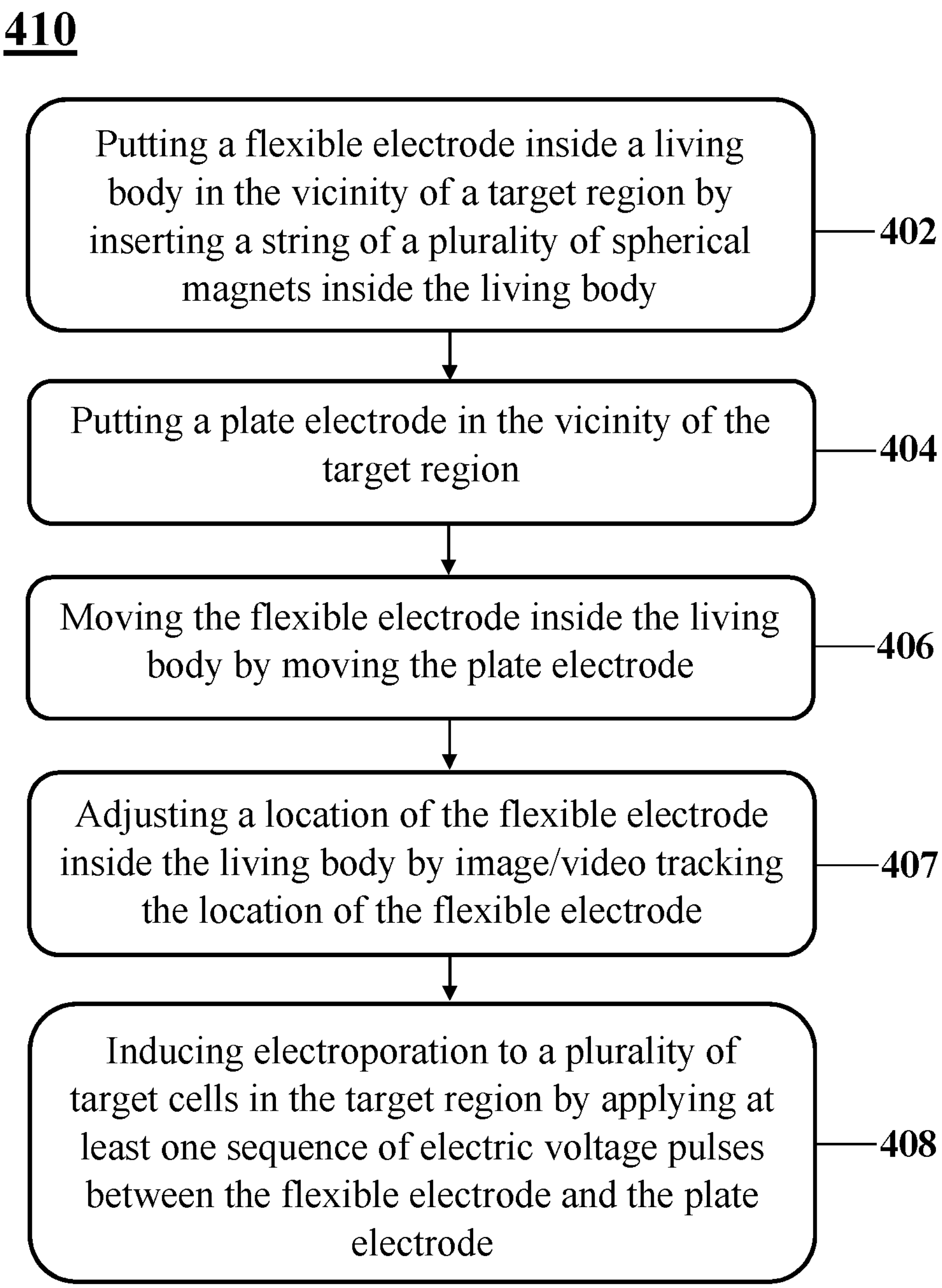
FIG. 4B shows an exemplary method for in-vivo electroporation of an exemplary plurality of target cells further including guiding a movement of an exemplary flexible electrode, consistent with one or more exemplary embodiments of the present disclosure.

FIG. 4A shows a method 400 for in-vivo electroporation of an exemplary plurality of target cells, consistent with one or more exemplary embodiments of the present disclosure. In an exemplary embodiment, method 400 may include putting a flexible electrode of an electroporation device inside a living body in the vicinity of a target region containing a plurality of target cells by inserting a string of a plurality of spherical magnets inside an exemplary living body (step 402), putting a plate electrode of an exemplary electroporation device in the vicinity of an exemplary target region (step 404), moving an exemplary flexible electrode inside an exemplary living body by moving an exemplary plate electrode (step 406), and inducing electroporation to an exemplary plurality of target cells by applying at least one sequence of electric voltage pulses between an exemplary flexible electrode and an exemplary plate electrode (step 406). In an exemplary embodiment, method 400 may further include guiding a movement of an exemplary flexible electrode inside an exemplary living body to be located at one or more target locations inside an exemplary living body. FIG. 4B shows a method 410 for in-vivo electroporation of an exemplary plurality of target cells further including guiding a movement of an exemplary flexible electrode, consistent with one or more exemplary embodiments of the present disclosure. In an exemplary embodiment, method 410 may include a step 407 of adjusting a location of an exemplary flexible electrode inside an exemplary living body by image/video tracking an exemplary location of an exemplary flexible electrode in addition to steps 402, 404, 406, and 408 of method 400. In an exemplary embodiment, methods 400 and 410 may be carried out utilizing electroporation device 300 and system 320. So, methods 400 and 410 may be described herein below in connection with FIGS. 3A-3C.

In further detail with respect to step 402, step 402 may include putting a flexible electrode of an electroporation device inside a living body in the vicinity of a target region containing a plurality of target cells by inserting a string of a plurality of spherical magnets inside an exemplary living body. In an exemplary embodiment, step 402 may include placing flexible electrode 302 in an exemplary living body in the vicinity of an exemplary target cells. In an exemplary embodiment, step 402 may include placing flexible electrode 302 in an exemplary target region of an exemplary living body containing an exemplary plurality of target cells. In an exemplary embodiment, an exemplary target cells may include a plurality of cancer cells, for example, colorectal cancer cells and/or esophageal cancer cells. In an exemplary embodiment, an exemplary target cells may include a plurality of cancer cells of a tumor mass. In an exemplary embodiment, step 402 may include placing flexible electrode 302 inside an exemplary target region. In an exemplary embodiment, an exemplary target region may include at least one of a tubular part, a lumen-shaped part, a cavity-shaped part, and combinations thereof of an exemplary living body. In an exemplary embodiment, an exemplary target region may include at least one of intestine, esophagus, vagina, and combinations thereof.

In an exemplary embodiment, step 402 of placing flexible electrode 302 in an exemplary target region of an exemplary living body may include inserting first spherical magnet 307 into an exemplary target region and adding a plurality of spherical magnets 306 to first spherical magnet 307 one by one up to reach an exemplary string of plurality of spherical magnets 306 with a length appropriate for generation of an exemplary electric field in the vicinity of an exemplary target cells. In an exemplary embodiment, camera 314 attached to first spherical magnet 307 may be inserted along with first spherical magnet 307 into an exemplary target region. In an exemplary embodiment, step 402 of placing flexible electrode 302 in an exemplary target region may include forming an exemplary string of plurality of spherical magnets 306 with or without camera 314 attached to first spherical magnet 307 inside an exemplary target region. In an exemplary embodiment, an exemplary length of string of plurality of spherical magnets 306 may be equal to a length of an exemplary target region to be treated by an electroporation process. In an exemplary embodiment, an exemplary length of string of plurality of spherical magnets 306 may be less than a length of colon. In an exemplary embodiment, last spherical magnet 308 of string of plurality of spherical magnets 306 may be attached to first distal end 310*a* of first electrically conductive line 310.

In further detail with respect to step 404, step 404 may include putting a plate electrode of an exemplary electroporation device in the vicinity of an exemplary target region. In an exemplary embodiment, step 404 may include placing plate electrode 304 in the vicinity of an exemplary target region. In an exemplary embodiment, placing plate electrode 304 in the vicinity of an exemplary target region may include placing plate electrode 304 within a distance of less than about 5 cm from an exemplary target region inside an exemplary living body or outside an exemplary living body. In an exemplary embodiment, placing plate electrode 304 in the vicinity of an exemplary target region may include placing plate electrode 304 over skin of an exemplary living body or inside an exemplary living body within a distance of less than about 5 cm from an exemplary target region. In an exemplary embodiment, placing plate electrode 304 in the vicinity of an exemplary target region may include placing plate electrode 304 in the vicinity of flexible electrode 302, which may be located inside an exemplary target region. In an exemplary embodiment, placing plate electrode 304 in the vicinity of an exemplary target region may include placing plate electrode 304 at a location within a distance in a range of about 0.5 mm to about 5 cm from flexible electrode 302.

In further detail with respect to step 406, step 406 may include moving an exemplary flexible electrode inside an exemplary living body by moving an exemplary plate electrode. In an exemplary embodiment, step 406 may include moving flexible electrode 302 inside an exemplary living body by moving plate electrode 304. In an exemplary embodiment, plate electrode 304 may be moved over skin of an exemplary living body; allowing for moving flexible electrode 302 inside an exemplary target region due to a magnetic field between plate electrode 304 and flexible electrode 302. In an exemplary embodiment, a location of flexible electrode 302 inside an exemplary living tissue may be adjusted by adjusting a location of plate electrode 304. In an exemplary embodiment, a path of movement of flexible electrode 302 from an insertion location of flexible electrode 302 into an exemplary living tissue to an exemplary target region, inside an exemplary target region, and bringing out from an exemplary target region/an exemplary living tissue may be adjusted by moving plate electrode 304 outside of an exemplary target region and/or living body. In an exemplary embodiment, a path of movement of flexible electrode 302 inside an exemplary target region may be controlled and adjusted by moving plate electrode 304; allowing for covering an exemplary path of flexible electrode 302 all over an exemplary target region. Therefore, an exemplary pulsed electric field applied between flexible electrode 302 and plate electrode 304 may be generated in all parts of an exemplary target region entirely.

In further detail with respect to step 407, step 407 may include adjusting a location of an exemplary flexible electrode inside an exemplary living body by image/video tracking an exemplary location of an exemplary flexible electrode. In an exemplary embodiment, step 407 may include tracking or monitoring an exemplary location of flexible electrode 302 inside an exemplary living body utilizing camera 314. In an exemplary embodiment, step 407 may include at least one of capturing an image from an exemplary target region, recording a video from an exemplary region, and combinations thereof utilizing camera 314 and receiving and analyzing at least one of captured image from an exemplary target region, recorded video from an exemplary region, and combinations thereof utilizing processing unit 322.

In further detail with respect to step 408, step 406 may include inducing electroporation to an exemplary plurality of target cells by applying at least one sequence of electric voltage pulses between an exemplary flexible electrode and an exemplary plate electrode. In an exemplary embodiment, step 408 may include inducing electroporation to an exemplary plurality of target cells by applying at least one sequence of electric voltage pulses between flexible electrode 302 and plate electrode 304. In an exemplary embodiment, applying at least one sequence of electric voltage pulses between flexible electrode 302 and plate electrode 304 may include applying at least one sequence of eight square-wave electric voltage pulses with a magnitude in a range of about 500 V/cm to about 1500 V/cm and a duration of about 100 μs between flexible electrode 302 and plate electrode 304.

In an exemplary embodiment, methods 400 and/or 410 may further include a step of injecting a drug or a therapeutical substance from a reservoir embedded in flexible electrode 302 or using an injection syringe into a location in the vicinity of/at an exemplary target region containing an exemplary plurality of target cells. In an exemplary embodiment, injecting an exemplary drug or an exemplary therapeutical substance to an exemplary location in the vicinity of/at an exemplary target region may be done intravenously. In an exemplary embodiment, an exemplary injected drug or therapeutical substance may penetrate into electroporated exemplary plurality of target cells; thereby, resulting in treating an exemplary plurality of target cells.

In an exemplary embodiment, steps 406 of moving flexible electrode 302 inside an exemplary living body by moving plate electrode 304, step 407 of tracking or monitoring an exemplary location of flexible electrode 302 inside an exemplary living body, and step 408 of applying at least one sequence of electric voltage pulses between flexible electrode 302 and plate electrode 304 may be done concurrently or iteratively in a cycle. In an exemplary embodiment, plate electrode 304 may be moved based on a tracked/monitored location of flexible electrode 302; allowing for adjusting an exemplary location of flexible electrode 302 inside an exemplary living body; thereby, an exemplary applied pulsed electric field may be generated over target parts of an exemplary living body, where an exemplary plurality of target cells may be present. Hence, total cells of an exemplary plurality of target cells may be electroporated via conducting exemplary methods 400 and/or 410.

Figure 5:
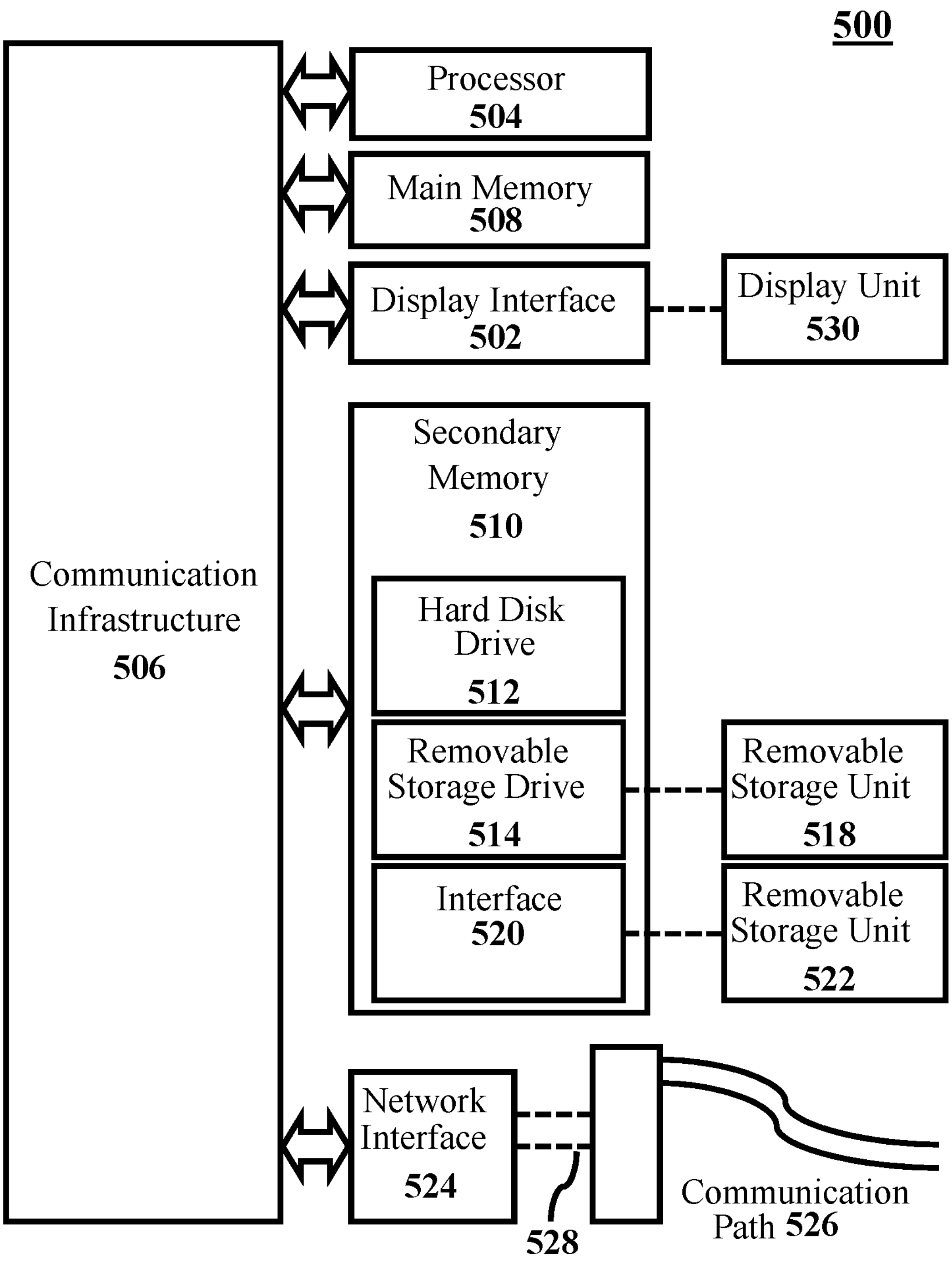
FIG. 5 shows an example computer system in which an embodiment of the present disclosure, or portions thereof, may be implemented as computer-readable code, consistent with one or more exemplary embodiments of the present disclosure.

FIG. 5 shows an example computer system 500 in which an embodiment of the present disclosure, or portions thereof, may be implemented as computer-readable code, consistent with one or more exemplary embodiments of the present disclosure. For example, computer system 500 may include an example of processing units 166 and/or 322, and steps 204 and 206 of flowchart presented in FIG. 2 and/or steps 407 and 408 of flowchart presented in FIGS. 4A-4B may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIGS. 1E, 2, 3C and 4A-4B.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor “cores”.

An embodiment of the present disclosure is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative embodiments, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in methods 200, 400, and 410 illustrated by FIGS. 2 and 4A-4B, discussed above. Accordingly, such computer programs represent controllers of computer system 500. Where an exemplary embodiment of methods 200, 400, and 410 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

Example 1: Tumor Destruction by In-Vivo Vacuum-Assisted Superficial Electroporation In this example, an exemplary system similar to system 160 was utilized to conduct an exemplary method similar to methods 200 described hereinabove for tumor destruction of BALB/C mice. All mice were tumorized by subcutaneous injection of 4T1 breast cancer cell line. Tumorized mice were classified to two groups, including a first group named as control group with no treatment applied to them and a second group named as treated group which were treated by inducing electroporation to tumor cells using exemplary system 160 and electroporation probe 100. Firstly, an electroporation probe similar to electroporation probe 100 was fabricated. The fabricated electroporation probe included two steel wire blades, each with a length of about 1 cm a distance of about 1 cm from each other. For treating the second mice group, firstly, Bleomycin was administered intratumorally using an appropriate dose; then, the two wire blades of the fabricated electroporation probe were put in contact with a region of tumor. Then, a pulsed electric field with a magnitude of 1000 V/cm including 8 electrical squared pulses with a time duration of about 100 μs and stopping duration of about 100 μs was applied to the two wire blades, and concurrently, a vacuum suction pressure of −0.7 Bar was applied to the treating region of tumor. The vacuum suction pressure was applied using a suction device in operating room as an example of vacuum device 164. For complete treatment of tumor, all parts of the tumor were scanned by the two wire blades and an exemplary treatment was repeated for each part.

Figure 6:
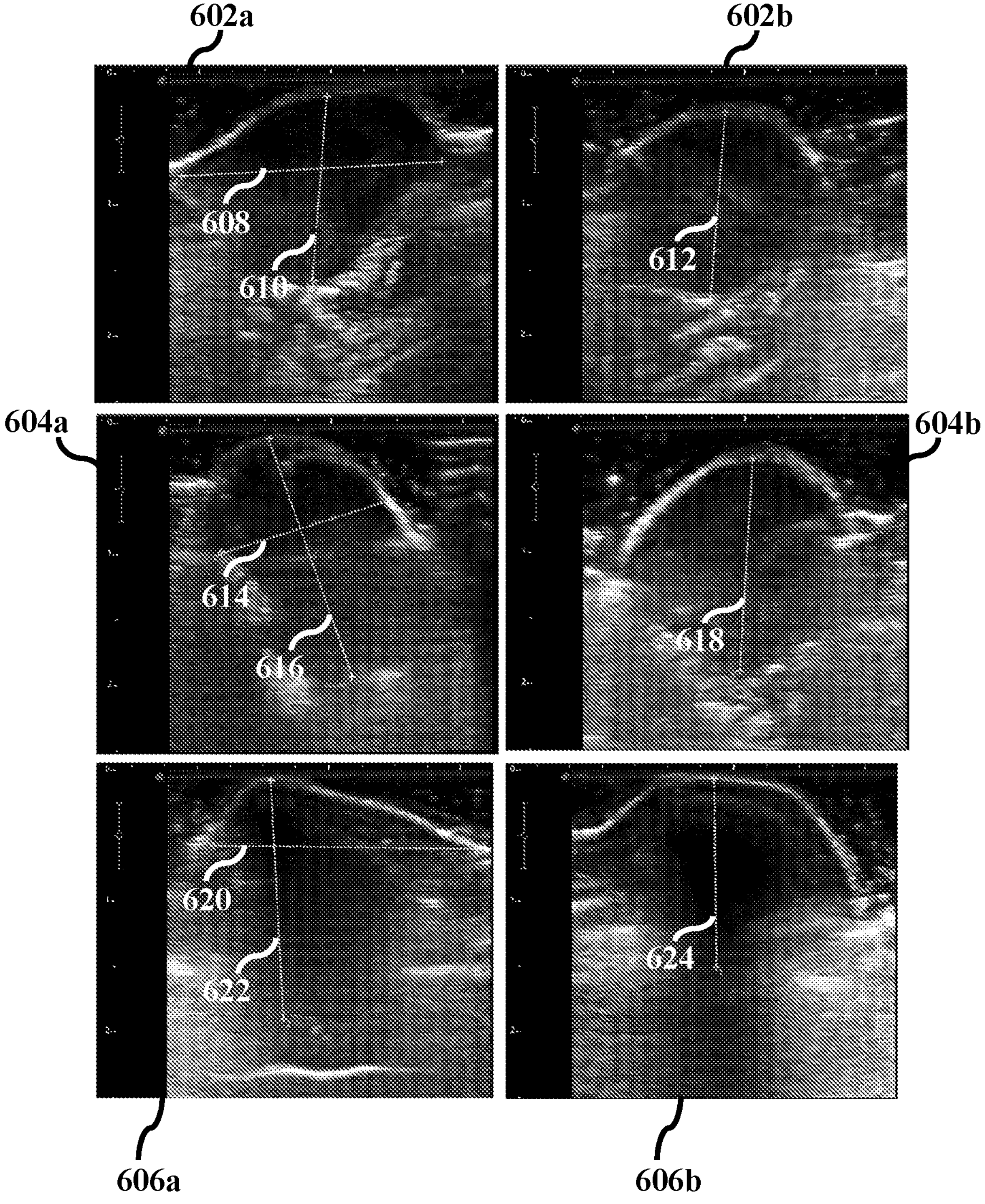
FIG. 6 shows images from two different views taken by a sonography device from an exemplary tumor of an exemplary mouse of control group initially and after 4 and 7 days, consistent with one or more exemplary embodiments of the present disclosure.

FIG. 6 shows images from two different views taken by a sonography device from an exemplary tumor of an exemplary mouse of control group initially and after 4 and 7 days, consistent with one or more exemplary embodiments of the present disclosure. Referring to FIG. 6, images 602*a* and 602*b* were taken initially from two sides of an exemplary tumor of a mouse in control group. Following up, images 604*a* and 604*b* were taken at the fourth day and images 606*a* and 606*b* were taken at the seventh day. Tumor dimensions are summarized in Table 1 with reference to FIG. 6 designated numbers.

TABLE 1

Tumor dimensions at days 0, 4, and 7 for an exemplary mouse of control group according to FIG. 6

| Day | Length (mm) |
|---|---|
| 0 | 408 = 14.07, 410 = 19.91, 412 = 14.46 |
| 4 | 414 = 19.26, 416 = 13.46, 418 = 16.27 |
| 7 | 420 = 20.06, 422 = 18.22, 424 = 14.41 |

Figure 7:
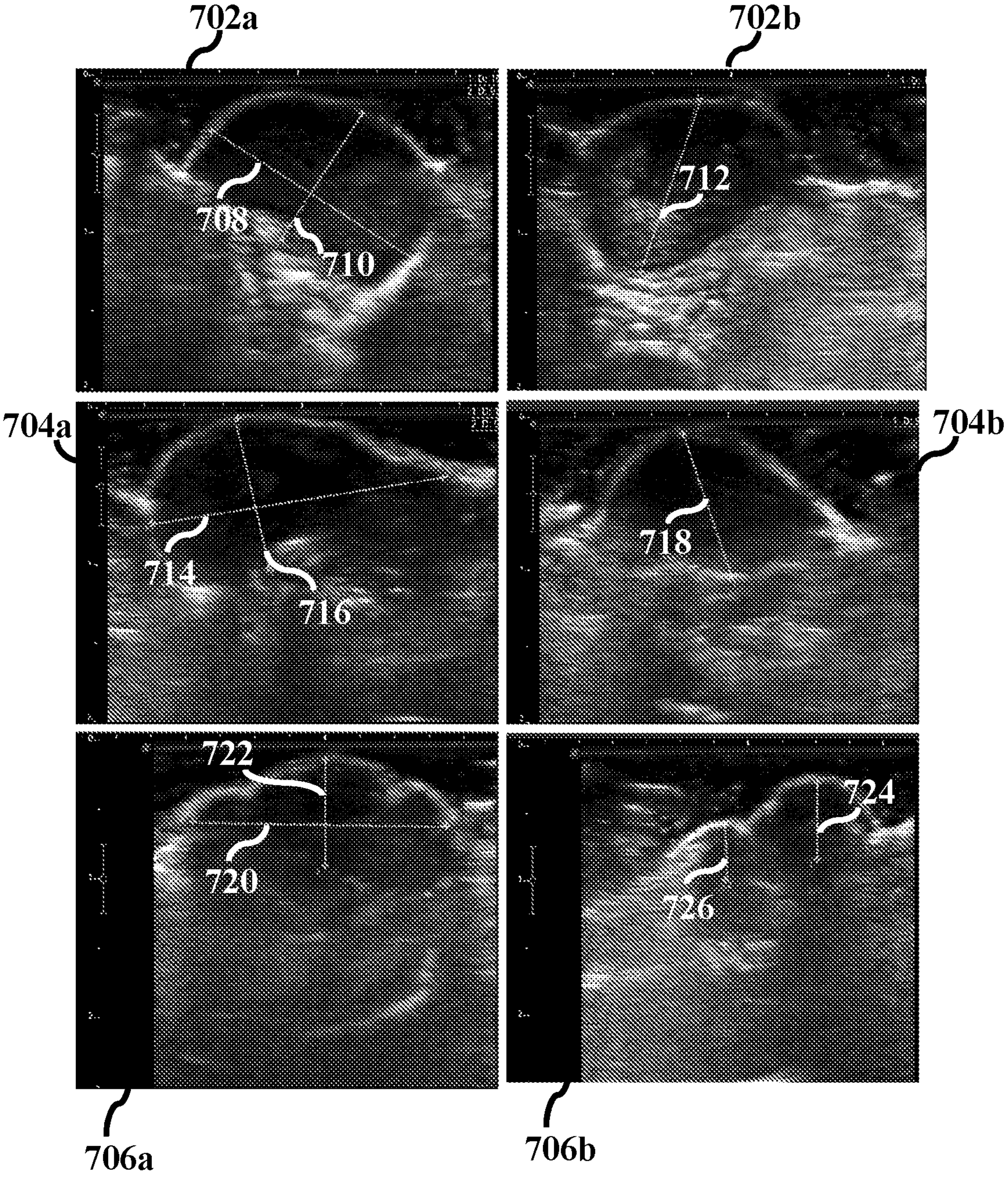
FIG. 7 shows images from two different views taken by a sonography device from an exemplary tumor of an exemplary mouse of treated group initially and after 4 and 7 days, consistent with one or more exemplary embodiments of the present disclosure.

FIG. 7 shows images from two different views taken by a sonography device from an exemplary tumor of an exemplary mouse of treated group initially and after 4 and 7 days, consistent with one or more exemplary embodiments of the present disclosure. Referring to FIG. 7, images 702*a* and 702*b* were taken initially from two sides of an exemplary tumor of a mouse in control group. Following up, images 704*a* and 704*b* were taken at the fourth day and images 706*a* and 706*b* were taken at the seventh day. Tumor dimensions are summarized in Table 2 with reference to FIG. 7 designated numbers.

TABLE 2

Tumor dimensions at days 0, 4, and 7 for an exemplary mouse of treated group according to FIG. 7

| Day | Length (mm) |
|---|---|
| 0 | 508 = 15.44, 510 = 9.56, 512 = 11.62 |
| 4 | 514 = 18.74, 516 = 9.78, 518 = 9.99 |
| 7 | 520 = 18.29, 522 = 7.64, 524 = 5.65, 526 = 4.07 |

Regarding FIGS. 6 and 7 and Tables 1 and 2, a significant reduction in size of the tumor in the treated group is clear, while this is not observed in the control group.

Example 2: In-Vivo Electroporation Using a Flexible String of Spherical Magnets Inside Body and a Plate Magnetic Electrode Outside In this example, an exemplary system similar to system 320 was utilized to apply an exemplary method similar to methods 400 and 410 described hereinabove to a New Zealand rabbit using an exemplary electroporation device fabricated similar to electroporation device 300 having two electrodes similar to flexible electrode 302 and plate electrode 304. An exemplary test was conducted to evaluate possible side effects of an exemplary electroporation method of rectosigmoid lumen including a region from rectum to rectosigmoid region in rabbits. At first, a rabbit was anesthetized and a number of spherical magnets as examples of plurality of spherical magnets 306 were entered the rabbit's rectum through its anus. The number of spherical magnets was increased until an exemplary flexible electrode, including the spherical magnets, reached the rectosigmoid region.

Figure 8:
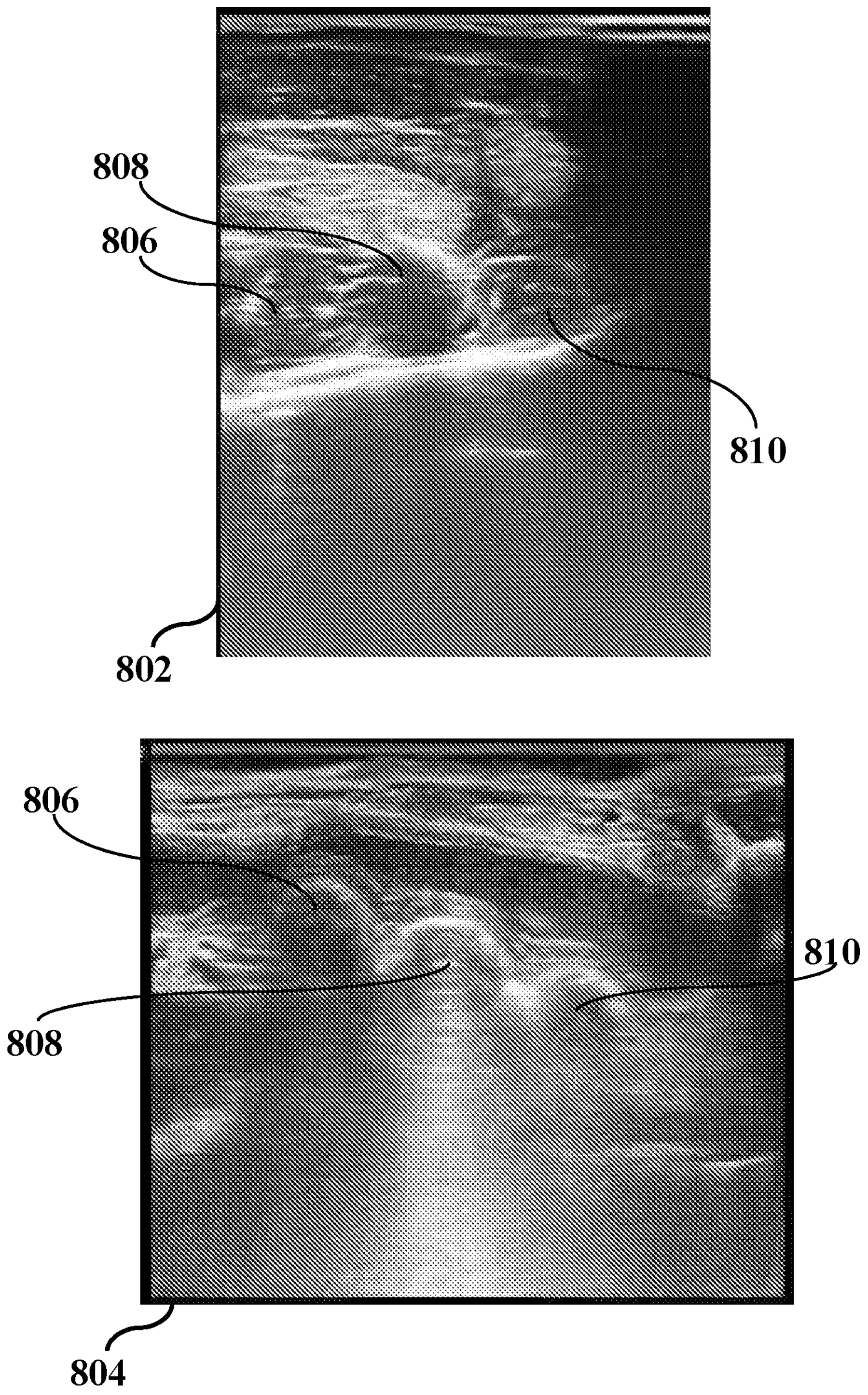
FIG. 8 shows ultrasound images from two different views from an exemplary large intestine of a rabbit representing a presence of exemplary spherical magnets of an exemplary flexible electrode there inside, consistent with one or more exemplary embodiments of the present disclosure.
Figure 9:
FIG. 9 shows computerized tomography (CT) scan images from rectum and rectosigmoid area of an exemplary rabbit after electroporation stimulation, consistent with one or more exemplary embodiments of the present disclosure.

FIG. 8 shows ultrasound images 802 and 804 from two different views from the large intestine of the rabbit representing a presence of spherical magnets 806-810 of the flexible electrode there inside, consistent with one or more exemplary embodiments of the present disclosure. After placing the flexible electrode in the desired area, a plate magnet was placed on the rabbit's stomach as the second electrode (so that the spherical magnets became close enough to each other and contact the colon wall from the inside) and electroporation stimulation with an intensity of 1000 V/cm was applied. The flexible electrode including the spherical magnets was moved along and inside all space of the large intestine of the rabbit by moving the plate magnet on the rabbit's stomach. After stimulation, the spherical magnets were removed one by one from the large intestine of the rabbit. After removing the spherical magnets, the stimulated area was washed with a sterile serum. The rabbit was subjected to a computerized tomography (CT) scan imaging 12 days after the stimulation, and no damage due to the introduction of the electrodes into the large intestine and electroporation stimulation in the rectum and rectosigmoid area was observed in terms of the CT scan as illustrated in FIG. 9.

INDUSTRIAL APPLICABILITY

Disclosed herein are devices for in-vivo electroporation of target cells in sensitive and/or difficult-to-access regions of a living body as well as systems and methods utilizing thereof. The devices include non-invasive structured electrodes capable of being placed in a target region or in the vicinity of the target region without causing bleeding, tearing, or any injuries.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for vacuum-assisted superficial electroporation, comprising:

a vacuum-assisted superficial electroporation probe, comprising:

an electrode mounting support comprising an enclosed container, the electrode mounting support comprising a top side and a bottom side, the top side comprising a singular hole and a plurality of pairs of holes, the bottom side comprising a plurality of apertures, each respective aperture being aligned to one of the singular hole and a pair of holes of the plurality of pairs of holes, each respective pair of holes of the top side and the respective aperture of the bottom side receiving one electrode passing there through, a path extending along the singular hole and an aperture of the plurality of apertures located along with the singular hole forming a hollow path configured to a vacuum pressure being applied there through; and at least two electrodes, each respective electrode comprising a wire blade protruding out from the bottom side of the electrode mounting support through an aperture of the plurality of apertures, each respective wire blade comprising a U-shaped wire comprising a flat base with two parallel lateral edges extending upwards from the flat base, a first lateral edge of the two parallel lateral edges passing through a first hole of a pair of holes of the plurality of pairs of holes and a second lateral edge of the two parallel lateral edges passing through a second hole of the pair of holes of the plurality of pairs of holes, an electrically conductive wire being welded to a first free end of the U-shaped wire and a second free end of the U-shaped wire being fixed onto the top side of the electrode mounting support, the at least two electrodes configured to transfer a pulsed electric field to a plurality of target cells by putting the flat base of the wire blade in contact with a zone of a tissue comprising the plurality of target cells;

an electrical pulse generator electrically connected to the at least two electrodes, an end of the electrically conductive wire being connected to the electrical pulse generator, the electrical pulse generator configured to apply a pulsed electric field to the at least two electrodes;

a vacuum device, comprising:

a vacuum tube comprising a flexible tube, the vacuum tube comprising a proximal end and a distal end, the distal end being fixed at a location on top of the hollow path, the vacuum tube configured to transfer a suction pressure to the plurality of target cells while the flat base of the wire blade being in contact with the zone of the tissue; and a vacuum pressure generator connected to the vacuum-assisted superficial electroporation probe via the vacuum tube, the proximal end of the vacuum tube being connected to the vacuum pressure generator, the vacuum pressure generator configured to apply the suction pressure through the vacuum tube; and a processing unit electrically connected to the electrical pulse generator and the vacuum pressure generator, the processing unit comprising:

a memory having processor-readable instructions stored therein; and a processor configured to access the memory and execute the processor-readable instructions, which, when executed by the processor configures the processor to perform a method, the method comprising:

tightening a contact between the respective flat bases of the at least two electrodes and the zone of the tissue by pulling the zone of the tissue towards the at least two electrodes via applying a vacuum pressure onto the zone of the tissue utilizing the vacuum pressure generator; and inducing electroporation to the plurality of target cells by applying at least one sequence of electric voltage pulses between the at least two electrodes utilizing the electrical pulse generator.

2. The system of claim 1, wherein the respective wire blades of the at least two electrodes are in parallel relation to each other with a distance in a range of 0.5 cm to 1.5 cm from each other.

3. The system of claim 1, wherein the flat base of each respective wire blade has a length in a range of 0.5 cm to 1.5 cm.

4. The system of claim 1, wherein a length in a range of 0.1 mm to 0.5 mm of each respective lateral edge of the two parallel lateral edges is protruded out from the bottom side of the electrode mounting support.

5. The system of claim 1, wherein the U-shaped wire comprises a biocompatible electrically conductive wire with a diameter in a range of 0.5 mm to 3 mm.

6. The system of claim 1, wherein:
- the singular hole is located at a center of the top side of the electrode mounting support; and
- the aperture of the plurality of apertures along with the singular hole is located at a center of the bottom side of the electrode mounting support.

7. The system of claim 1, further comprising a cap being fixed on top of the electrode mounting support, the cap comprising:
- a first outlet receiving the electrically conductive wire passing there through;
- a second outlet receiving the vacuum tube being fixed thereon; and
- a bottom surface comprising an opening located along with the hollow path and the second outlet, wherein the opening receives the electrically conductive wire passing there through.

8. The system of claim 1, wherein applying the vacuum pressure onto the zone of the tissue comprises applying a vacuum pressure with a magnitude in a range of −0.5 bar to −0.7 bar at the proximal end of the vacuum tube utilizing the vacuum pressure generator.

9. The system of claim 1, wherein applying the at least one sequence of electric voltage pulses between the at least two electrodes comprises applying at least one sequence of eight square-wave electric voltage pulses with a magnitude in a range of 500 V/cm to 1500 V/cm and a duration of 100 μs between the at least two electrodes.

10. A system for in-vivo electroporation of a plurality of target cells in a target region of a living body, comprising:
- an electroporation device, configured to transfer a pulsed electric field to the plurality of target cells, the electroporation device comprising:
  - a flexible electrode with a variable length, the flexible electrode comprising a string of a plurality of spherical magnets connected in series, the variable length of the flexible electrode being adjustable by adding or removing one or more spherical magnets, the flexible electrode being put inside the living body in the vicinity of the target region; and
  - a plate electrode being put in the vicinity of the target region, the plate electrode comprising a plate magnet or a ferromagnetic steel plate, the flexible electrode being movable inside the living body by moving the plate electrode;
- an electrical pulse generator electrically connected to the electroporation device, the electrical pulse generator configured to apply a pulsed electric field between the flexible electrode and the plate electrode; and
- a processing unit electrically connected to the electrical pulse generator, the processing unit comprising:
  - a memory having processor-readable instructions stored therein; and
  - a processor configured to access the memory and execute the processor-readable instructions, which, when executed by the processor configures the processor to perform a method, the method comprising:
    - inducing electroporation to the plurality of target cells by applying at least one sequence of electric voltage pulses between the flexible electrode and the plate electrode utilizing the electrical pulse generator.

11. The system of claim 10, wherein each spherical magnet of the plurality of spherical magnets comprises a spherical magnet with a diameter in a range of 0.5 cm to 2 cm.

12. The system of claim 10, wherein the plate electrode comprises a plate with a surface area in a range of 10 $cm^2$ to 30 $cm^2$ and a thickness in a range of 2 mm to 5 mm.

13. The system of claim 10, wherein the plate electrode is located outside of the target region, the plate electrode being located over skin of the living body or inside the living body within a distance of less than 5 cm from the target region.

14. The system of claim 10, wherein a distance between the plate electrode and the flexible electrode is within a range of 0.5 mm to 5 cm.

15. The system of claim 10, wherein the flexible electrode is put inside the target region, the flexible electrode being located inside at least one of intestine, esophagus, vagina, stomach, duodenum, colon, cervix, uterus, and combinations thereof.

16. The system of claim 10, further comprising a camera attached to a first spherical magnet of the string of the plurality of spherical magnets, the camera being electrically connected to the processing unit, the camera being configured to at least one of capture an image from the target region, record a video from the target region, and combinations thereof.

17. The system of claim 16, wherein the method further comprises:
- tracking a location of the flexible electrode by at least one of capturing an image from the target region, recording a video from the target region, and combinations thereof utilizing the camera, the tracked location of the flexible electrode being utilized for placing the flexible electrode at a target location by moving the plate electrode.

18. The system of claim 10, wherein applying the at least one sequence of electric voltage pulses between the flexible electrode and the plate electrode comprises applying at least one sequence of eight square-wave electric voltage pulses with a magnitude in a range of 500 V/cm to 1500 V/cm and a duration of 100 μs between the flexible electrode and the plate electrode.

19. The system of claim 10, further comprising two electrically conductive lines, comprising:
- a first electrically conductive line, comprising a first distal end and a first proximal end, the first distal end being connected to a last spherical magnet of the string of the plurality of spherical magnets, the first proximal end being connected to a first pole of the electrical pulse generator; and
- a second electrically conductive line, comprising a second distal end and a second proximal end, the second distal end being connected to the plate electrode, the first proximal end being connected to a second pole of the electrical pulse generator.

* * * * *